US012702692B2

(12) United States Patent
Sandoz et al.

(10) Patent No.: US 12,702,692 B2
(45) Date of Patent: Aug. 11, 2026

(54) THERAPEUTIC USE OF CALCIUM-ACTIVATED CHLORIDE CHANNEL PEPTIDE ACTIVATOR

(71) Applicants: CENTRE NATIONAL DE LA RECHERCHE SCIENTIFIQUE, Paris (FR); UNIVERSITE COTE D'AZUR, Nice Cedex (FR); INSTITUT NATIONAL DE LA SANTÉ ET DE LA RECHERCHE MÉDICALE, Paris (FR)

(72) Inventors: Guillaume Sandoz, Antibes (FR); Pablo Avalos Prado, Nice (FR); Jacques Barhanin, Nice (FR)

(73) Assignees: CENTRE NATIONAL DE LA, Paris (FR); RECHERCHE SCIENTIFIQUE UNIVERSITÉ CÔTE D'AZUR, Nice (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 712 days.

(21) Appl. No.: 18/012,290

(22) PCT Filed: Jul. 9, 2021

(86) PCT No.: PCT/EP2021/069217
§ 371 (c)(1),
(2) Date: Dec. 22, 2022

(87) PCT Pub. No.: WO2022/008738
PCT Pub. Date: Jan. 13, 2022

(65) Prior Publication Data

US 2023/0242610 A1 Aug. 3, 2023

(30) Foreign Application Priority Data

Jul. 10, 2020 (EP) .................................... 20305795

(51) Int. Cl.
*A61P 43/00* (2006.01)
*A61K 38/10* (2006.01)

(52) U.S. Cl.
CPC .............. *A61K 38/10* (2013.01); *A61P 43/00* (2018.01)

(58) Field of Classification Search
CPC ........ C07K 14/705; A61P 43/00; A61P 27/02; A61K 38/00
See application file for complete search history.

(56) References Cited

U.S. PATENT DOCUMENTS 5,620,892 A * 4/1997 Kurtz .................. C07K 14/705 435/255.2
6,458,542 B1 * 10/2002 George, Jr. ........ G01N 33/6872 536/24.31

(Continued)

FOREIGN PATENT DOCUMENTS

CN 105 106 228 A 12/2015
WO 0114403 A1 3/2001

(Continued)

OTHER PUBLICATIONS

GenBank ABS31134.1, voltage gated potassiun channel accessory subunit isoform 3, partial [*Homo sapiens*], ncbi.nlm.nih.gov, 1 page (Jul. 23, 2016), also available at https://www.ncbi.nlm.nih.gov/protein/ABS31134.1 (last visited Sep. 29, 2025) (Year: 2016).*

(Continued)

*Primary Examiner* — Randall L Beane
(74) *Attorney, Agent, or Firm* — Maier & Maier, PLLC

(57) ABSTRACT

The present disclosure relates to a calcium-activated chloride channel peptide activator and its therapeutic use.

1 Claim, 10 Drawing Sheets

Figure 1:
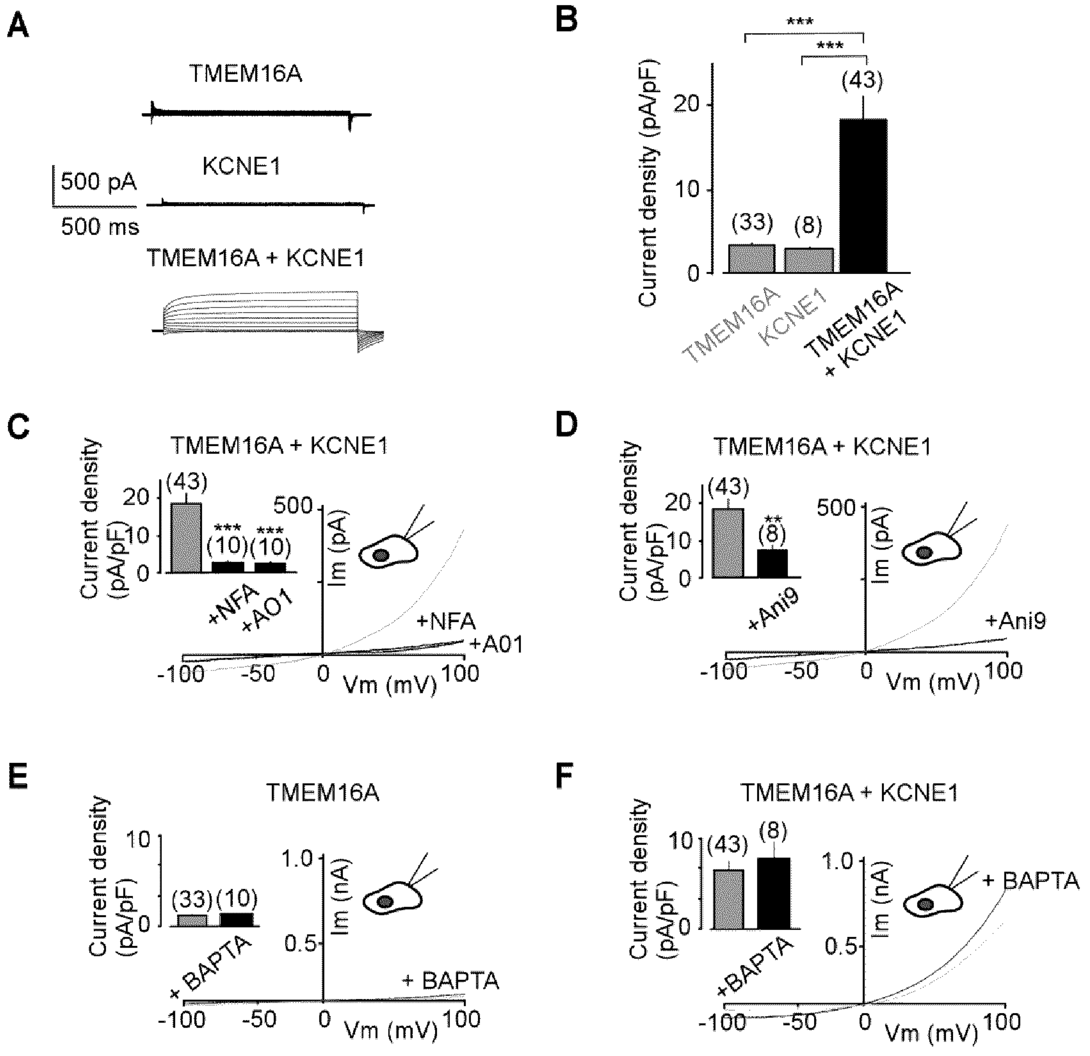

Specification includes a Sequence Listing.

A hN13 sequence
LARRSPRSSDGKL hS38G sequence
LARRSPRSGDGKL

(56) References Cited

U.S. PATENT DOCUMENTS

| | | | |
|---|---|---|---|
| 2003/0108924 | A1 | 6/2003 | George, Jr. |
| 2009/0227469 | A1 | 9/2009 | Conklin |

FOREIGN PATENT DOCUMENTS

| | | | |
|---|---|---|---|
| WO | 0127323 A1 | 4/2001 |
| WO | 03016504 A2 | 2/2003 |
| WO | 2013/022793 A1 | 2/2013 |
| WO | 2017/193059 A1 | 11/2017 |
| WO | 2018/202471 A1 | 11/2018 |

OTHER PUBLICATIONS

Jeon et al: "Expression and immunohistochemical localization of TMEM16A/anoctamin 1, a calcium-activated chloride channel in the mouse cochlea", Cell and Tissue Research, vol. 345, No. 2, p. 223-230, Jul. 21, 2011.

Uniprot; "UniParc—UPI0001593950", Jul. 24, 2007.

* cited by examiner

SEQUENCE LISTING

```
<160> NUMBER OF SEQ ID NOS: 7

<210> SEQ ID NO 1
<211> LENGTH: 9
<212> TYPE: PRT
<213> ORGANISM: artificial sequence
<220> FEATURE:
<223> OTHER INFORMATION: amino acid residues between positions 30 to 38
      of the human KCNE1 protein sequence

<400> SEQUENCE: 1

Leu Ala Arg Arg Ser Pro Arg Ser Ser
1               5


<210> SEQ ID NO 2
```

<211> LENGTH: 13
<212> TYPE: PRT
<213> ORGANISM: Artificial Sequence
<220> FEATURE:
<223> OTHER INFORMATION: amino acid residues between positions 30 to 42 of the human KCNE1 protein sequence

<400> SEQUENCE: 2

```
Leu Ala Arg Arg Ser Pro Arg Ser Ser Asp Gly Lys Leu
1               5                   10
```

<210> SEQ ID NO 3
<211> LENGTH: 9
<212> TYPE: PRT
<213> ORGANISM: Artificial Sequence
<220> FEATURE:
<223> OTHER INFORMATION: TMEM16-A activator peptide "1
<220> FEATURE:
<221> NAME/KEY: misc_feature
<222> LOCATION: (4)..(4)
<223> OTHER INFORMATION: X is Arginine, Lysine or histidine
<220> FEATURE:
<221> NAME/KEY: misc_feature
<222> LOCATION: (6)..(6)
<223> OTHER INFORMATION: X is proline or glutamine
<220> FEATURE:
<221> NAME/KEY: misc_feature
<222> LOCATION: (7)..(7)
<223> OTHER INFORMATION: X is arginine or leucine
<220> FEATURE:
<221> NAME/KEY: misc_feature
<222> LOCATION: (8)..(8)
<223> OTHER INFORMATION: X is serine or arginine
<220> FEATURE:
<221> NAME/KEY: misc_feature
<222> LOCATION: (9)..(9)
<223> OTHER INFORMATION: X is serine or aspartic acid

<400> SEQUENCE: 3

```
Leu Ala Arg Xaa Ser Xaa Xaa Xaa Xaa
1               5
```

<210> SEQ ID NO 4
<211> LENGTH: 13
<212> TYPE: PRT
<213> ORGANISM: Artificial Sequence
<220> FEATURE:
<223> OTHER INFORMATION: TMEM16A peptide activator #2
<220> FEATURE:
<221> NAME/KEY: misc_feature
<222> LOCATION: (4)..(4)
<223> OTHER INFORMATION: X is arginine, lysine or histidine
<220> FEATURE:
<221> NAME/KEY: misc_feature
<222> LOCATION: (6)..(6)
<223> OTHER INFORMATION: X is proline or glutamine
<220> FEATURE:
<221> NAME/KEY: misc_feature
<222> LOCATION: (7)..(7)
<223> OTHER INFORMATION: X is arginine or leucine
<220> FEATURE:
<221> NAME/KEY: misc_feature
<222> LOCATION: (8)..(8)
<223> OTHER INFORMATION: X is serine or arginine
<220> FEATURE:
<221> NAME/KEY: misc_feature
<222> LOCATION: (9)..(9)
<223> OTHER INFORMATION: X is serine or aspartic acid
<220> FEATURE:
<221> NAME/KEY: misc_feature
<222> LOCATION: (11)..(11)
<223> OTHER INFORMATION: X is glycine or serine

<400> SEQUENCE: 4

-continued

```
Leu Ala Arg Xaa Ser Xaa Xaa Xaa Xaa Asp Xaa Lys Leu
1               5                   10


<210> SEQ ID NO 5
<211> LENGTH: 13
<212> TYPE: PRT
<213> ORGANISM: Artificial sequence
<220> FEATURE:
<223> OTHER INFORMATION: hN13 S38G

<400> SEQUENCE: 5

Leu Ala Arg Arg Ser Pro Arg Gly Gly Asp Gly Lys Leu
1               5                   10


<210> SEQ ID NO 6
<211> LENGTH: 13
<212> TYPE: PRT
<213> ORGANISM: Artificial sequence
<220> FEATURE:
<223> OTHER INFORMATION: amino acid residues between positions 30 to 42
      of the rat KCNE1 protein sequence

<400> SEQUENCE: 6

Leu Ala Arg Arg Ser Gln Leu Arg Asp Asp Ser Lys Leu
1               5                   10


<210> SEQ ID NO 7
<211> LENGTH: 13
<212> TYPE: PRT
<213> ORGANISM: Artificial Sequence
<220> FEATURE:
<223> OTHER INFORMATION: Synthetic scramble peptide

<400> SEQUENCE: 7

Leu Leu Ala Lys Arg Gly Arg Asp Ser Gly Pro Ser Arg
1               5                   10
```

THERAPEUTIC USE OF CALCIUM-ACTIVATED CHLORIDE CHANNEL PEPTIDE ACTIVATOR

SEQUENCE LISTING

This document incorporates by reference an electronic sequence listing file, which was electronically submitted along with this document. The text file is named 2026-01-02_13500176US_seqlisting.txt, is 3067 bytes, and was created on Jan. 2, 2026.

FILED OF THE INVENTION

The present disclosure relates to a calcium-activated chloride channel peptide activator and its therapeutic use.

BACKGROUND

Calcium-activated chloride channels (CaCCs) belonging to the Anoctamin protein superfamily play a major role in cell physiology, including signal transduction, regulation of cardiac and neuronal excitability, epithelial secretion and muscle contraction, among others (Hartzell et al., 2005; Pedemonte and Galietta, 2014). Given this broad range of functions, chloride channel dysfunction leads to a large spectrum of diseases. These diverse pathologies include cystic fibrosis, salivary gland dysfunction, such as in Sjogren's syndrome and caused by radiation injury, dry eye syndrome, dry mouth, gastrointestinal hypomotility disease and cardiac arrythmia.

TMEM16A was first member of this superfamily to be identified (Caputo et al., 2008; Schroeder et al., 2008; Yang et al., 2008). The structure of TMEM16A was recently elucidated, defining the channel as homodimer consisting of ten transmembrane domains per subunit with an extensive intracellular domain that adopts a ferredoxin-like folding (Dang et al., 2017). Nevertheless, no β-subunit has been identified for this channel up to now.

Several TMEM16A agonists have been identified. For instance, a functional cell-based screen of small-molecule collections allows to identify small molecules reported to activate TMEM16A (Namkung, W. et al. FASEB J. 2011, 25, 4048-4062; WO2013/002793). However, these compounds may be unable to activate endogenous TMEM16A in cells (Centeio R. et al. Int. J. Mol. Sci. 2020, 21, 2557).

Thus, it remains a need to discover new compounds that specifically activate $Ca^{2+-}$ activated chloride channel independently of the presence of calcium and produce sustained activation of $Cl^-$ conductance.

KCNE1 is a 129-residue peptide, with a single short hydrophobic plasma membrane spanning domain and carboxy- and amino-terminal domains facing towards the intracellular and extracellular side, respectively (Takumi, T., et al. 2018, Science, 242, 1042-1045). When injected in Xenopus oocytes, KCNE1 produces a slowly activating $K^+$ current (Takumi, T., et al. 2018, Science, 242, 1042-1045). For this reason, KCNE1 was initially believed to be the minimal sequence that could encode for a $K^+$ channel (Goldstein, S. A., and Miller, C. 1991, Neuron 7, 403-408; Wang, K. W., and Goldstein, S. A. 1995. Neuron 14, 1303-9). Experiments in other heterologous cell models questioned this finding since expression of KCNE1 alone is not able to induce currents in mammalian cell lines (Lesage, F., et al. 1993, Receptors Channels, 1, 143-152). This enigma was resolved by the discovery that Xenopus oocytes express endogenous KCNQ1 channels, which are modulated by KCNE1 (Barhanin, J. et al. 1996. Nature 384, 78-80; Sanguinetti, M. C. et al. 1996, Nature 384, 80-83). These experiments showed that KCNE1 is not encoding for an α-subunit but for an ancillary (β) subunit of the voltage-dependent potassium KCNQ1 channel that underlies the slow repolarizing component in cardiac action potential (IKs) (Barhanin, J. et al. 1996. Nature 384, 78-80; Sanguinetti, M. C. et al. 1996, Nature 384, 80-83). In addition to the $K^+$ current described above, a voltage-dependent $Cl^-$ current was observed upon injection of cRNA of KCNE1 in Xenopus oocytes (Attali, B. et al. 1993. Nature 365, 850-852), and up to now, the molecular identity of this current remained elusive.

SUMMARY OF THE INVENTION

The inventors hypothesized that KCNE1 serves as a β-subunit of the pore forming TMEM16A subunits to induce the KCNE1-induced $Cl^-$ current, described 30 years ago (Attali, B. et al. 1993. Nature 365, 850-852), not anymore gated by $Ca^{2+}$ but exclusively by voltage. Using electrophysiology in heterologous and native systems and single molecule pulldown assays, the inventors demonstrate that KCNE1 interacts physically with TMEM16A, inducing a sustained voltage-dependent chloride current in the absence of increased cytoplasmic $Ca^{2+}$. Importantly, the inventors found that clinically relevant inherited polymorphisms within the KCNE1-regulating domain, including the common S38G polymorphism, abolish the KCNE1-dependent regulation of TMEM16A, indicating that this current may contribute to inherited pathologies.

The present invention relates to a TMEM16A peptide activator for use as a medicament comprising or consisting of the sequence L-A-R-X1-S-X2-X3-X4-X5 (SEQ ID NO: 3) wherein said X1 is arginine, lysine or histidine; X2 is proline or glutamine; X3 is arginine or leucine; X4 is serine or arginine and X5 is glycine or aspartic acid.

In particular, the peptide comprises or consists of the sequence L-A-R-X1-S-X2-X3-X4-X5-D-X6-K-L (SEQ ID NO: 4) wherein said X1 is arginine, lysine or histidine, X2 is proline or glutamine, X3 is arginine or leucine, X4 is serine or arginine, X5 is glycine or aspartic acid and X6 is glycine or serine.

In the preferred embodiment, said peptide for use according to the present invention comprises the amino acid sequence L-A-R-R-S-PR-S-S (SEQ ID NO: 1) or a functional variant thereof, more preferably amino acid sequence L-A-R-R-S-PR-S-S-D-G-K-L (SEQ ID NO: 2) or a functional variant thereof. In another preferred embodiment, said peptide is of 8 to 100 amino acids residues, preferably 8 to 20 amino acids residues, more preferably 13 to 20 amino acids residues. The peptide for use according to the present invention comprises or consists of an amino sequence which is at least 90% identical to an amino acids sequence of: SEQ ID NO: 1 or 2, more particularly comprises or consists of an amino acid sequence comprising or consisting of an amino acid sequence having no more than 3 conservative substituted amino acids residues as compared to SEQ ID NO: 1 or 2.

In another aspect, the present invention relates to a nucleic acid or an expression vector comprising said nucleic acid encoding the peptide as described above for use as medicament.

In a preferred embodiment, the peptide, nucleic acid or expression vector is for use in the treatment of diseases caused by chloride channel dysfunction, preferably diseases caused by TMEM16-A channel dysfunction, more preferably selected from the group consisting of: cystic fibrosis, dry mouth, dry eye syndrome, cardiac arrhythmia and gastrointestinal hypomobility disease, preferably dry eye syndrome.

In another aspect, the present invention also relates to a pharmaceutical composition comprising the peptide, nucleic acid or expression vector as described above and a pharmaceutically acceptable carrier. The present invention also relates to the peptide of 8 to 100 amino acids residues, preferably 8 to 20 amino acids residues, more preferably 13 to 20 amino acids residues comprising an amino sequence of SEQ ID NO: 1 or 2 or an amino sequence which is at least 90% identical to an amino acids sequence of: SEQ ID NO: 1 or 2.

Finally, the present invention also relates to the use of the peptide, the nucleic acid or the expression vector as described above as a chloride channel activator.

FIGURE LEGENDS

FIG. 1. KCNE1 converts the CaCC TMEM16A into a voltage-dependent chloride channel. (A) Representative current traces showing the effect of expression of either KCNE1 or TMEM16A or both TMEM16A and KCNE1 in HEK293T cells. Traces were generated using pulses between −100 and +100 mV at 20 mV intervals from a holding potential of −80 mV. (B) Summary of current densities obtained at +100 mV. (C-D) Representative traces showing the effect of application of either niflumic acid (NFA, 100 μM, C), T16A(inh) A01 (10 μM, C) or Ani9 (300 nM, D). (E-F) Representative traces of TMEM16A alone (E) or co-expressed with KCNE1 (F) in the presence of 1 mM of BAPTA. Currents were elicited by voltage-ramps (from −100 to +100 mV, 1 s duration), insets show a summary of current densities obtained at +100 mV. Mann-Whitney test (p<0.01, *p<0.001). Mean±SEM.

Figure 2:
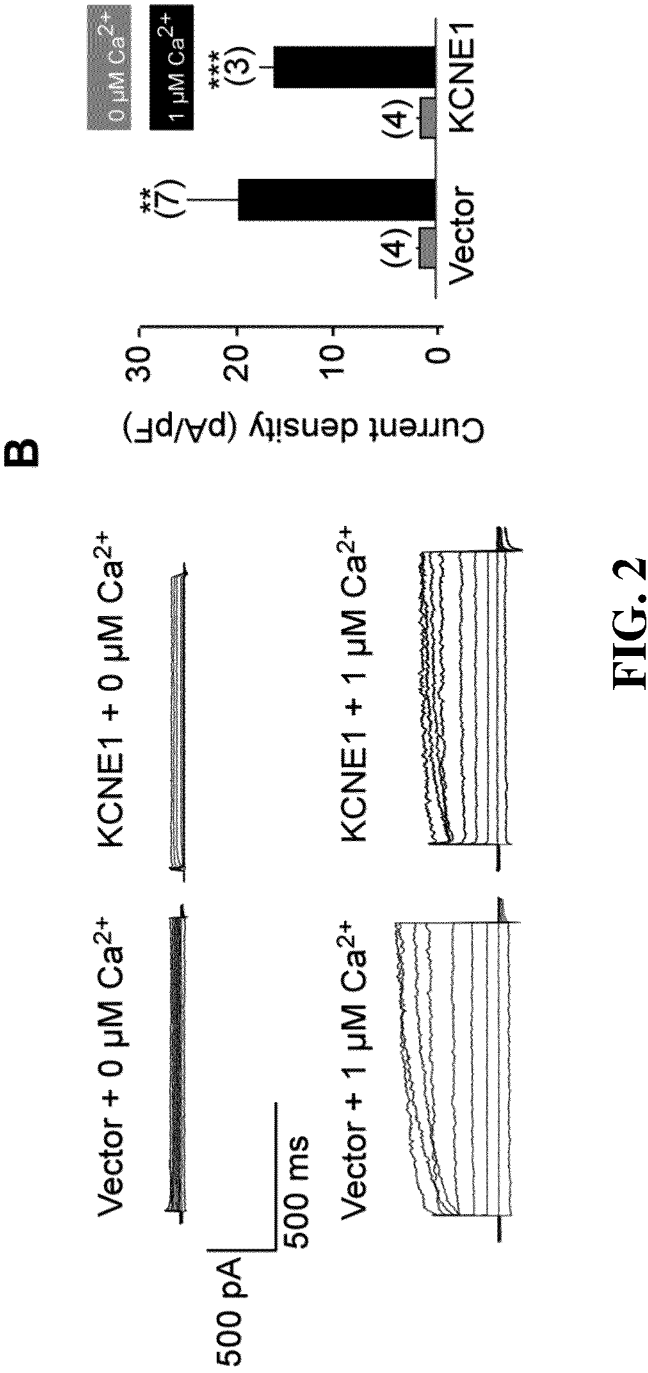

FIG. 2. KCNE1 expression does not lead to an increase of intracellular $Ca^{2+}$. (A) Representative current traces obtained from HEK293T cells transfected with SK4 and either an empty vector or KCNE1 at different $Ca^{2+}$ concentrations. SK4 current is not activated by KCNE1 coexpression showing the absence of intracellular calcium increase. Traces were generated using pulses between −100 and +100 mV from a holding potential at −80 mV. (B) Summary of current densities obtained at +100 mV. Mann-Whitney test (p<0.05, *p<0.001). Mean±SEM.

Figure 3:
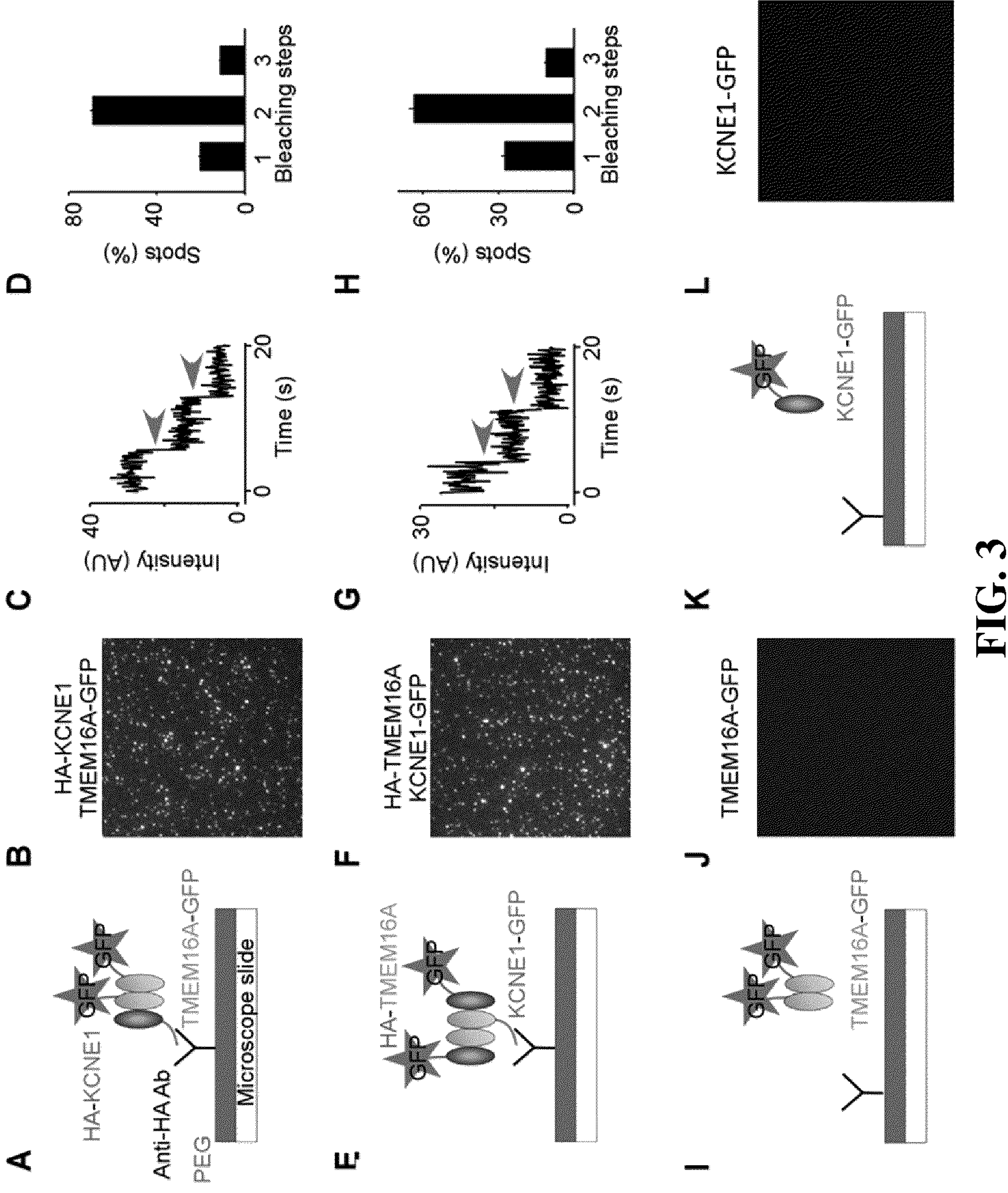

FIG. 3. KCNE1 and TMEM16A interact in a 2α:2β complex. (A) Schematic of single molecule pulldown (SiMPull) assay of TMEM16A. Lysates of HEK293T cells co-expressing TMEM16A-GFP and HA-tagged KCNE1 were immobilized on a PEG-passivated coverslip conjugated to a biotinylated anti-HA antibody. (B) Representative TIRF image of single molecules showing the pulldown of TMEM16A-GFP by HA-KCNE1. (C) Representative trace showing two photobleaching steps (red arrows) of TMEM16A-GFP (AU, for Arbitrary Units). (D) Summary of photobleaching step distribution for TMEM16A-GFP. (E-H), same as (A-D) for the SiMPull of KCNE1-GFP by HA-TMEM16A. (I-L) Specificity of the anti-HA antibody. (I-J) SiMPull assay with TMEM16A-GFP in the absence of HA-KCNE1. (K-L) SiMPull assay with KCNE1-GFP in the absence of HA-TMEM16A.

Figure 4:
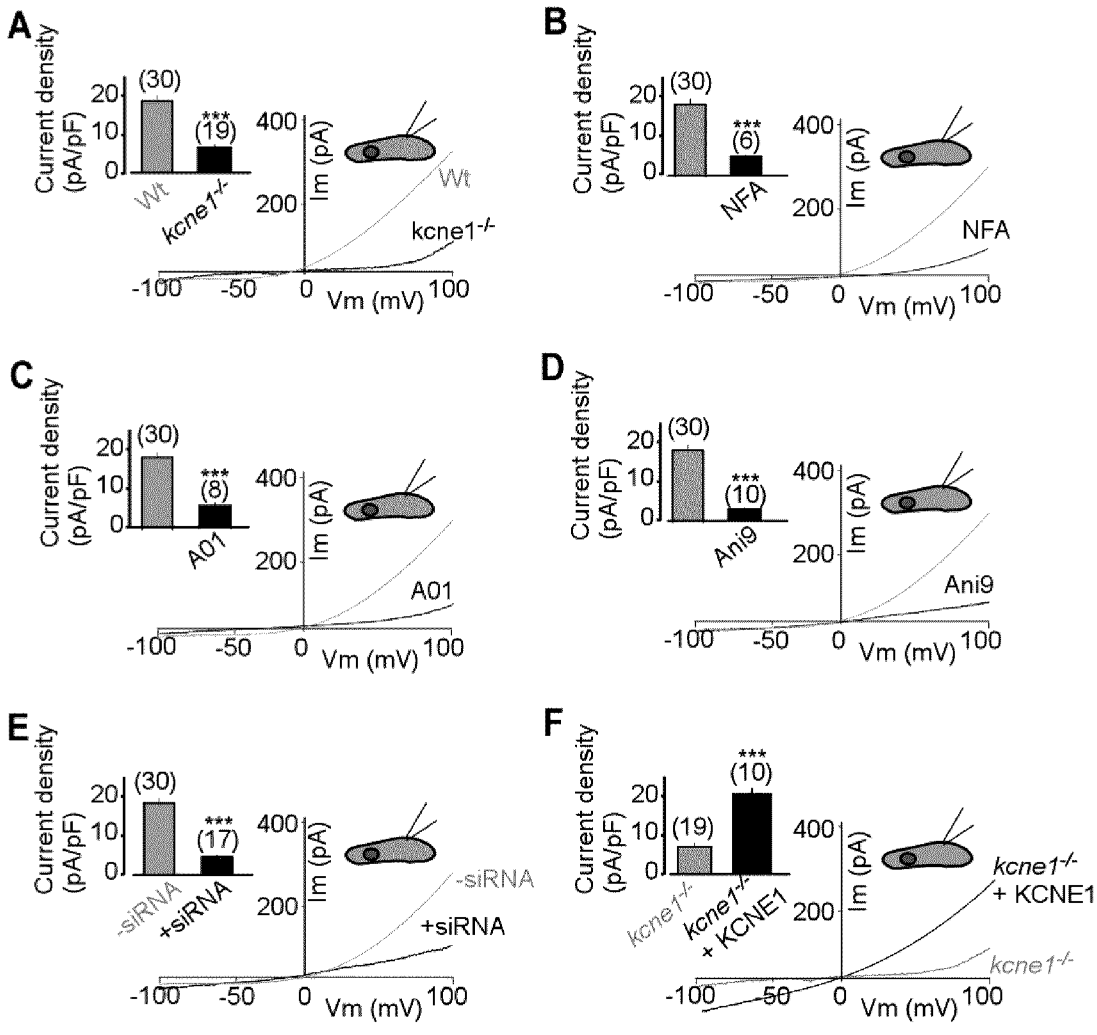

FIG. 4. KCNE1-TMEM16A complex creates a voltage-dependent chloride current in proximal convoluted tubule (PCT) cells. (A) Representative traces obtained from wild type and $kcne1^{-/-}$ PCT cells. (B-D) Representative traces from wild type cells after incubation with NFA (100 μM, B), A01 (10 μM, C), Ani9 (5 μM, D). (E) Trace obtained after transfection with siRNA against TMEM16A. (F) Trace obtained from a $kcne1^{-/-}$ PCT cell after transfection with KCNE1 cDNA. Currents were generated by voltage-ramps (from −100 to +100 mV, 1 s duration). Insets show current densities. Mann-Whitney test (***p<0.001). Mean±SEM.

Figure 5:
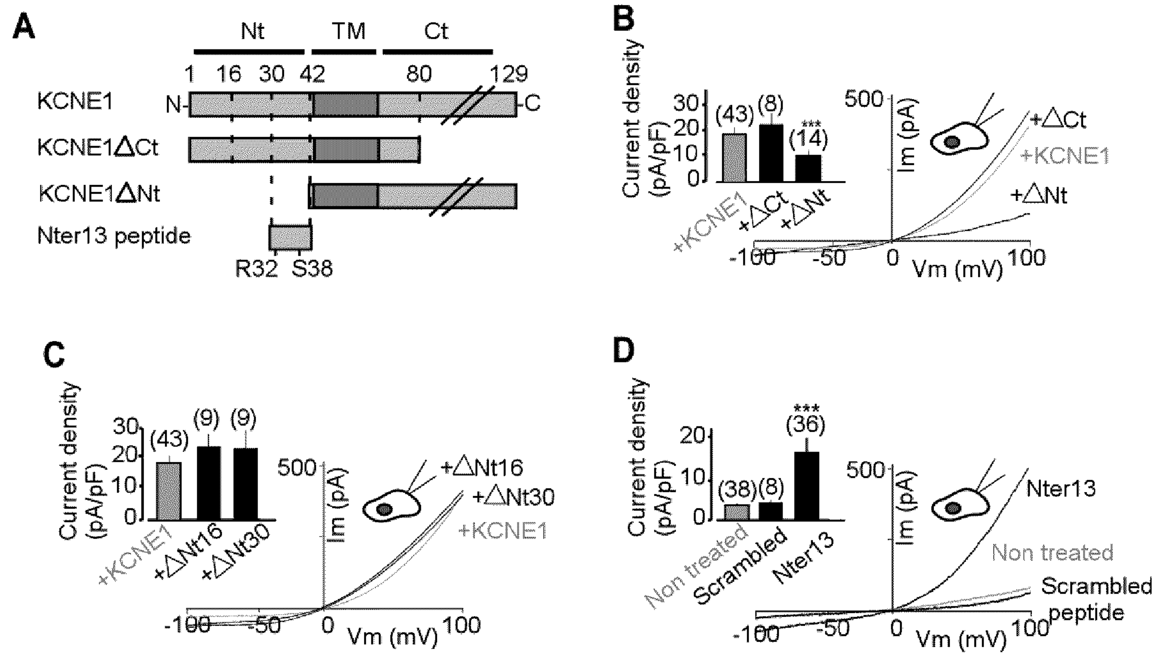

FIG. 5. The pre-transmembrane domain (Nter13) of KCNE1 is sufficient for KCNE1-induced TMEM16A conversion. (A) Cartoon depicting KCNE1 truncated forms used to determine the domains implicated in TMEM16A interaction. (B-C) Representative traces obtained from HEK293T cells co-expressing TMEM16A and KCNE1ΔCt, KCNE1ΔNt (B), KCNE1ΔNt16 or KCNE1ΔNt30 (C). (D) Representative traces showing the effect of the Nter13 and a scrambled peptide on a HEK293T cell expressing TMEM16A alone. Currents were elicited by voltage-ramps (from −100 to +100 mV, 1 s duration). Insets show the summary of current densities obtained for the different conditions at +100 mV. Mann-Whitney test (***p<0.001). Mean±SEM.

Figure 6:
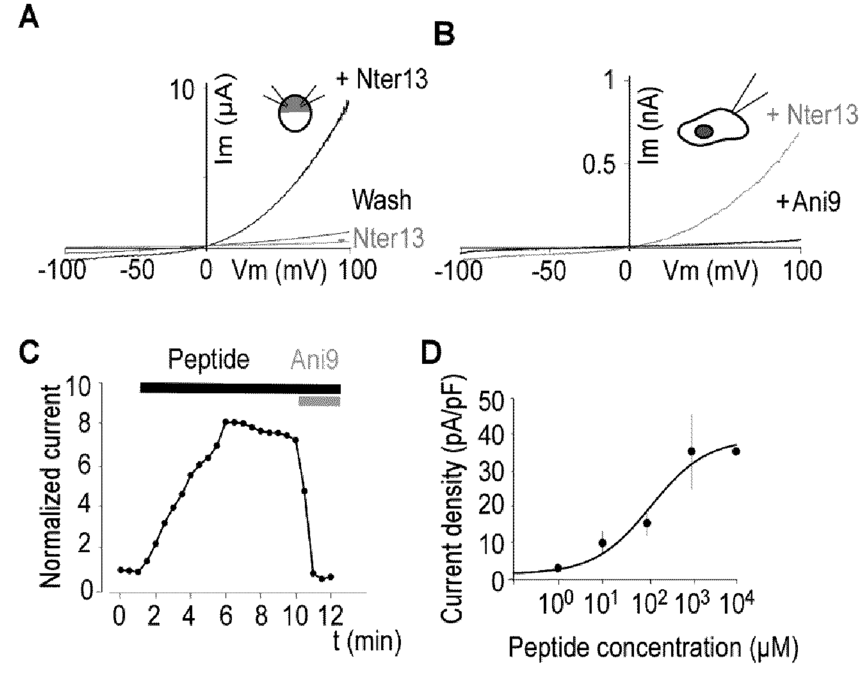

FIG. 6. Nter13 peptide is sufficient to switch the functioning mode of TMEM16A. (A) Representative current traces from a Xenopus oocyte, expressing endogenously TMEM16A, obtained after application of the Nter13 peptide (100 μM) and wash-out. (B) Representative traces showing the effect of Nter13 peptide application (100 μM) and its reversion by Ani9 (5 μM) on a HEK293T cell expressing TMEM16A alone. (C) Effect of Nter13 peptide on TMEM16A current over time followed by inhibition through co-application of Ani9 in HEK293T cells. (D) Concentration-response curve representing the current density observed for different peptide concentrations in HEK293T cells expressing TMEM16A. Mean±SEM.

Figure 7:
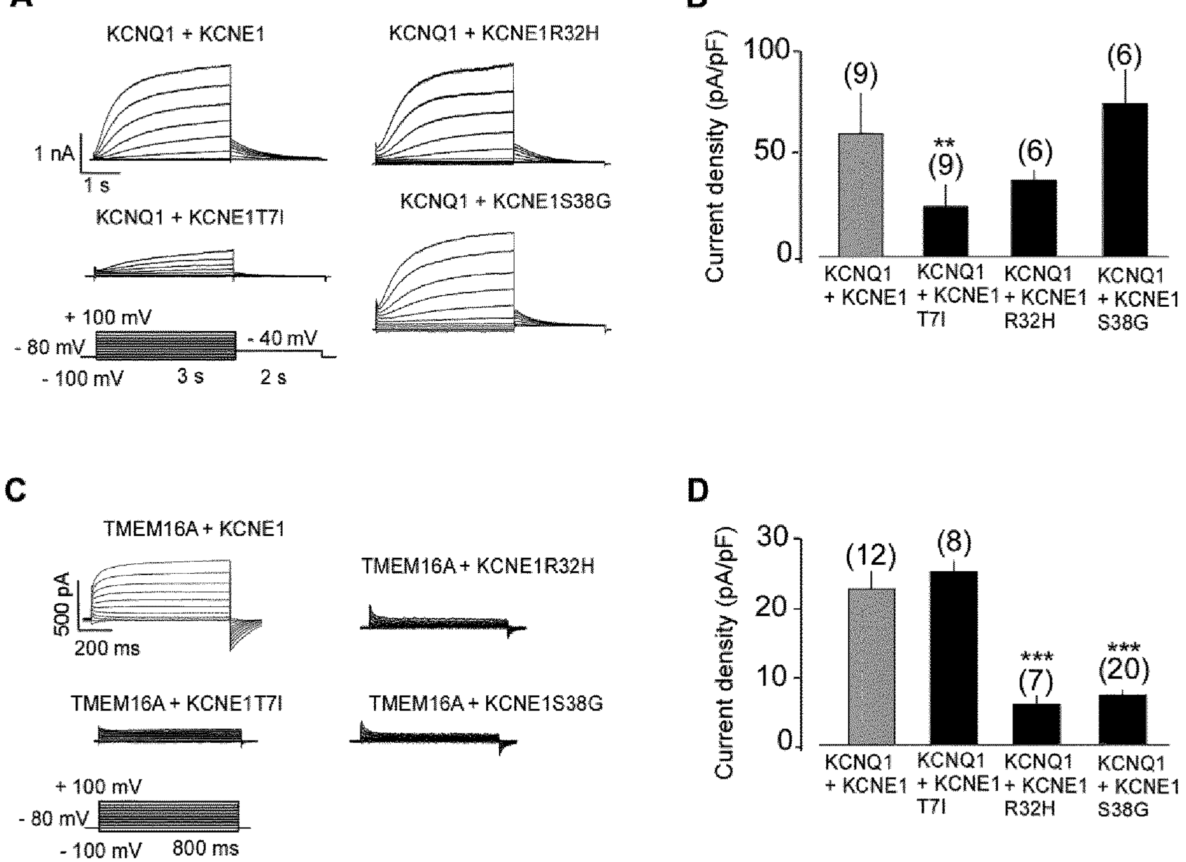

FIG. 7. The KCNE1 S38G and R32H do not impair the KCNQ1 regulation, but abolish TMEM16A regulation. (A) Current traces of whole-cell patch-clamp recordings from cells transfected with wild type KCNQ1 alone and co-transfected with KCNE1 or KCNE1R32H or KCNE1S38G. (B) Summary of current densities obtained for the different conditions at +40 mV. (C-D) Same as A-B, with cells co-expressing KCNE1 and TMEM16A. Current densities were calculated at +100 mV. Mann-Whitney test (p<0.05, *p<0.001). Mean±SEM.

Figure 8:
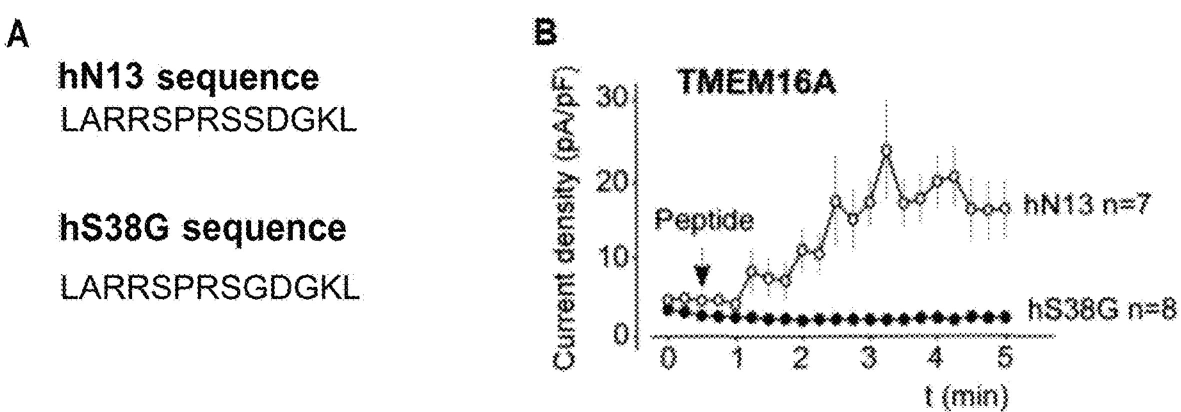

FIG. 8: hS38G peptide has no effect on TMEM16A. (A) Comparison of hN13 (SEQ ID NO: 2) and hS38G sequences (SEQ ID NO: 5). (B) Perfusion of either hN13 (100 μM) or hS38G (100 μM) on HEK293T cells expressing TMEM16A. Currents were elicited by voltage-ramps (from −100 mV to +100 mV, 1 s duration) and currents taken at +100 mv. Mean±SEM.

Figure 9:
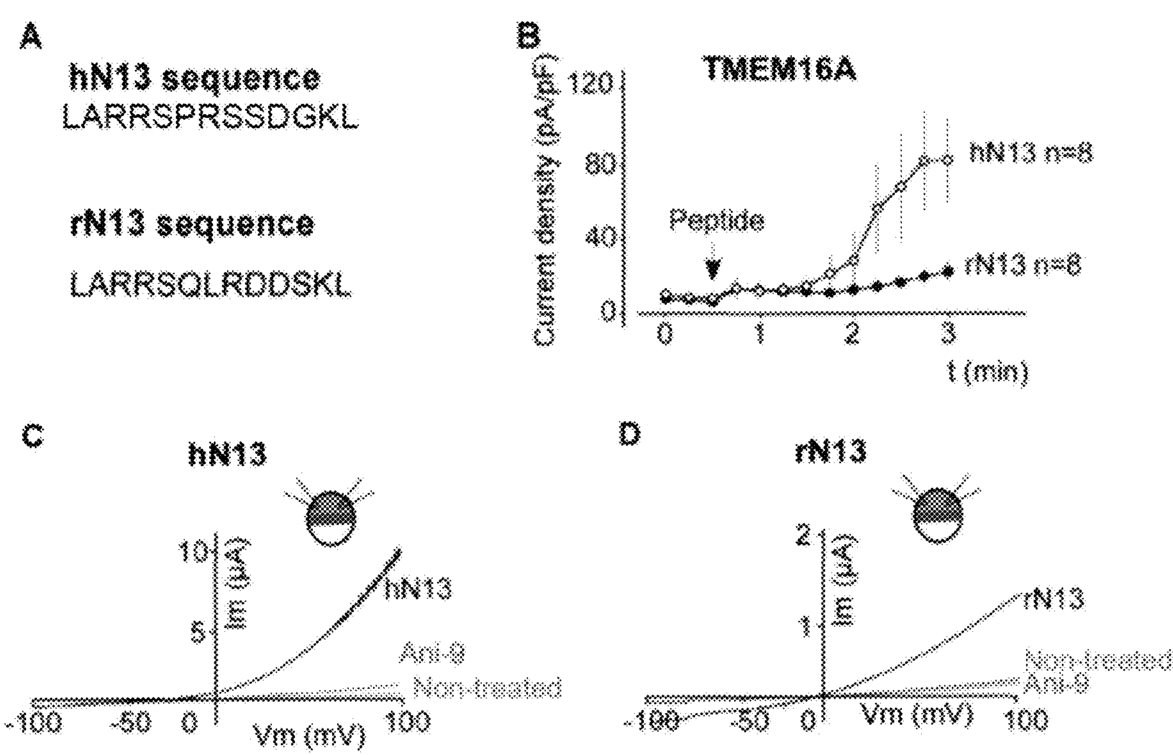

FIG. 9: hN13 peptide is more potent than rN13 on TMEM16A. (A) Comparison of hN13 (SEQ ID NO: 2) and rN13 sequences (SEQ ID NO: 6). (B) Perfusion of either hN13 (100 μM) or rN13 (100 μM) on HEK293T cells expressing TMEM16A. (C-D) Representative currents showing the effect of either hN13 (100 μM, C) or rN13 (100 μM, D) perfusion on Xenopus oocytes, followed by application of Ani-9 (5 μM). Currents were elicited by voltage-ramps (from −100 mV to +100 mV, 1 s duration) and currents taken at +100 mv. Mean±SEM.

Figure 10:
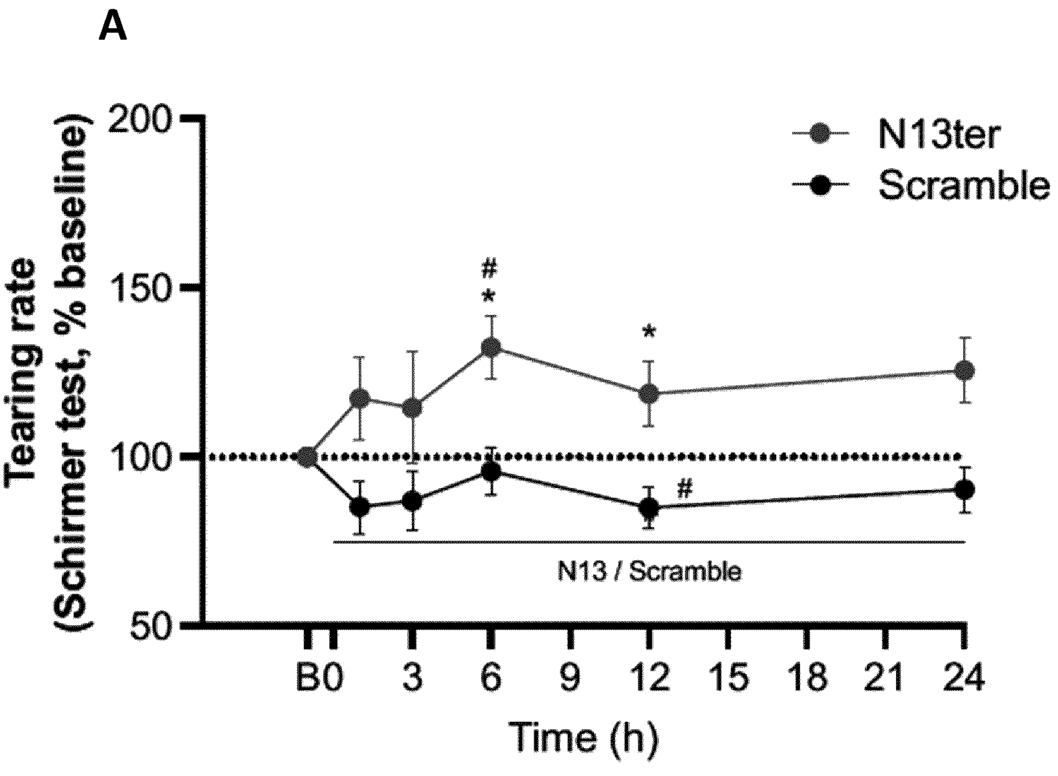
Figure 10:
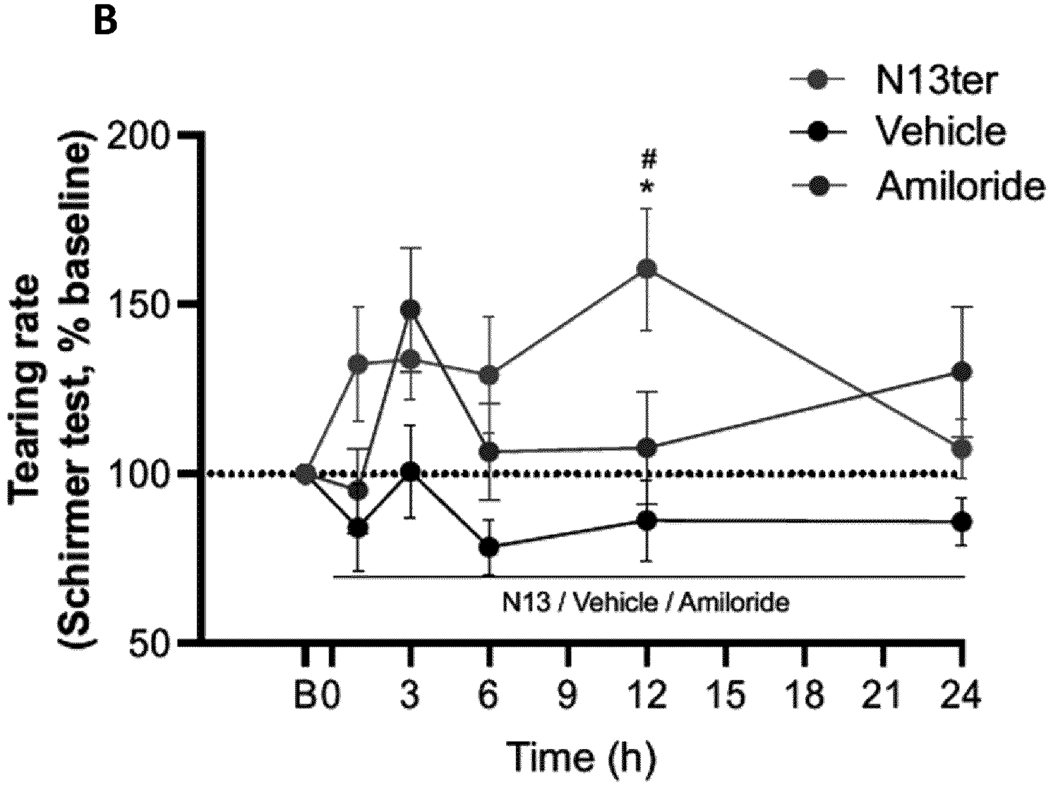

FIG. 10. Comparison of effects of N13ter, vehicle, amiloride and scramble peptide on tearing rate. For comparison purposes, data has been normalized to basal tearing rate (100%) for each eye and averaged in each group. A) N13ter or Scramble peptide (both at 10 mM) were topically applied at 0 h and tearing rate was measured at 1, 3, 6, 12 and 24 h. N13ter (n=20 eyes; 10 rats); Scramble (n=20 eyes; 10 rats). *p<0.05 vs. Scramble group; Two-way ANOVA plus Bonferroni post-tests. #p<0.05 vs. Basal; One-way ANOVA plus Bonferroni post-tests. B) B (Basal tearing rate). PBS, amiloride (1 mM) or N13ter (10 mM) were topically applied at 0 h and tearing rate was measured at 1, 3, 6, 12 and 24 h. Vehicle (n=14 eyes, 14 rats), amiloride (n=14 eyes, 7 rats), N13ter (n=12 eyes; 6 rats). *p<0.05 N13 vs. Vehicle group; Two-way ANOVA plus Bonferroni post-tests. #p<0.05 vs. Basal; One-way ANOVA plus Bonferroni post-tests.

Figure 11:
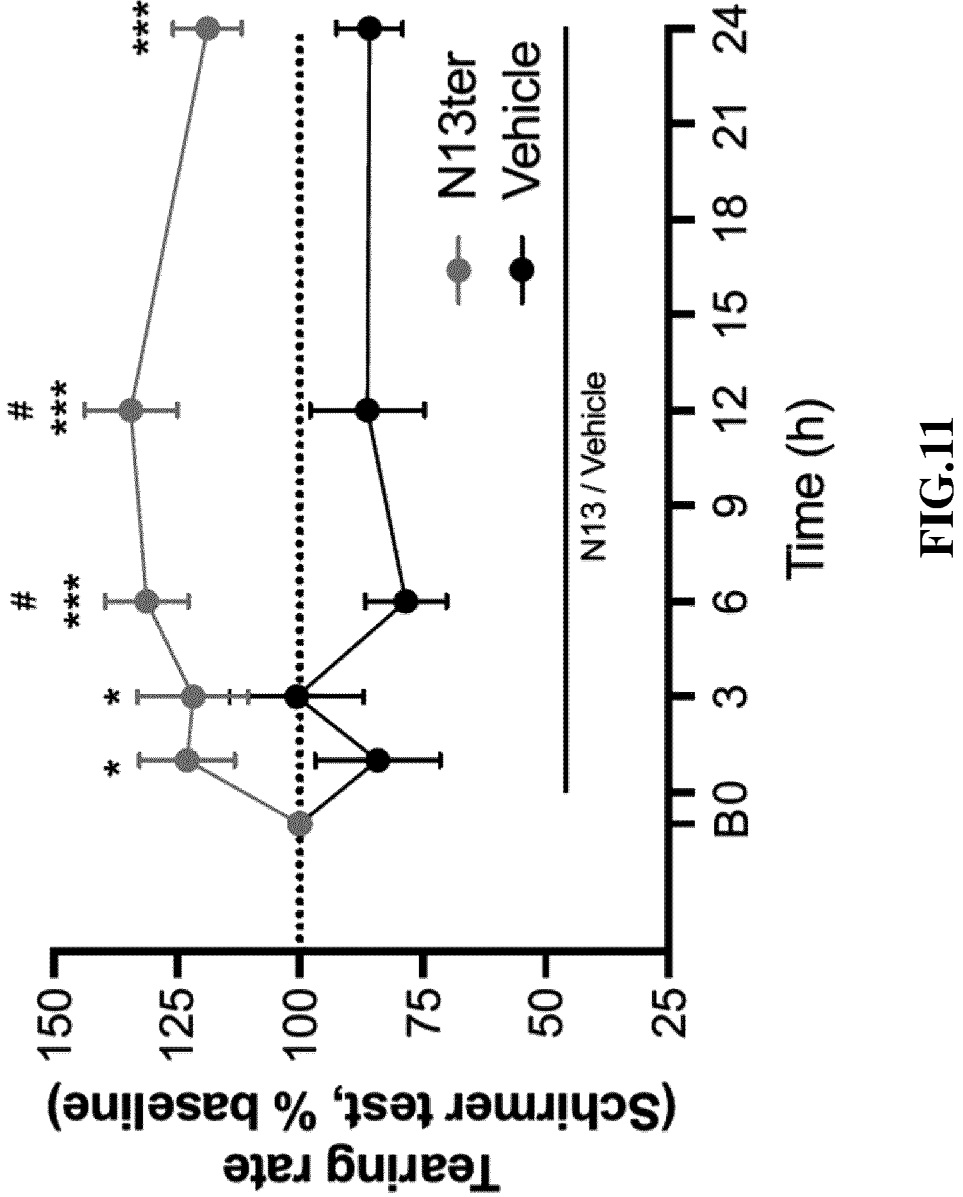

FIG. 11: Comparison of acute effects of N13ter vs vehicle on tearing rate. All data on different studies assaying N13ter peptide (10 mM) has been pull together in a single group (n=32 eyes from 16 rats). Vehicle group (n=14 eyes form 7 rats). For comparison purposes, data has been normalized to basal tearing rate (100%) for each eye and averaged in each group. *p<0.05; ***p<0.001; N13ter vs. Vehicle group; Two-way ANOVA plus Bonferroni post-tests. #p<0.05 N13ter vs. Basal (B); One-way ANOVA plus Bonferroni post-tests.

Figure 12:
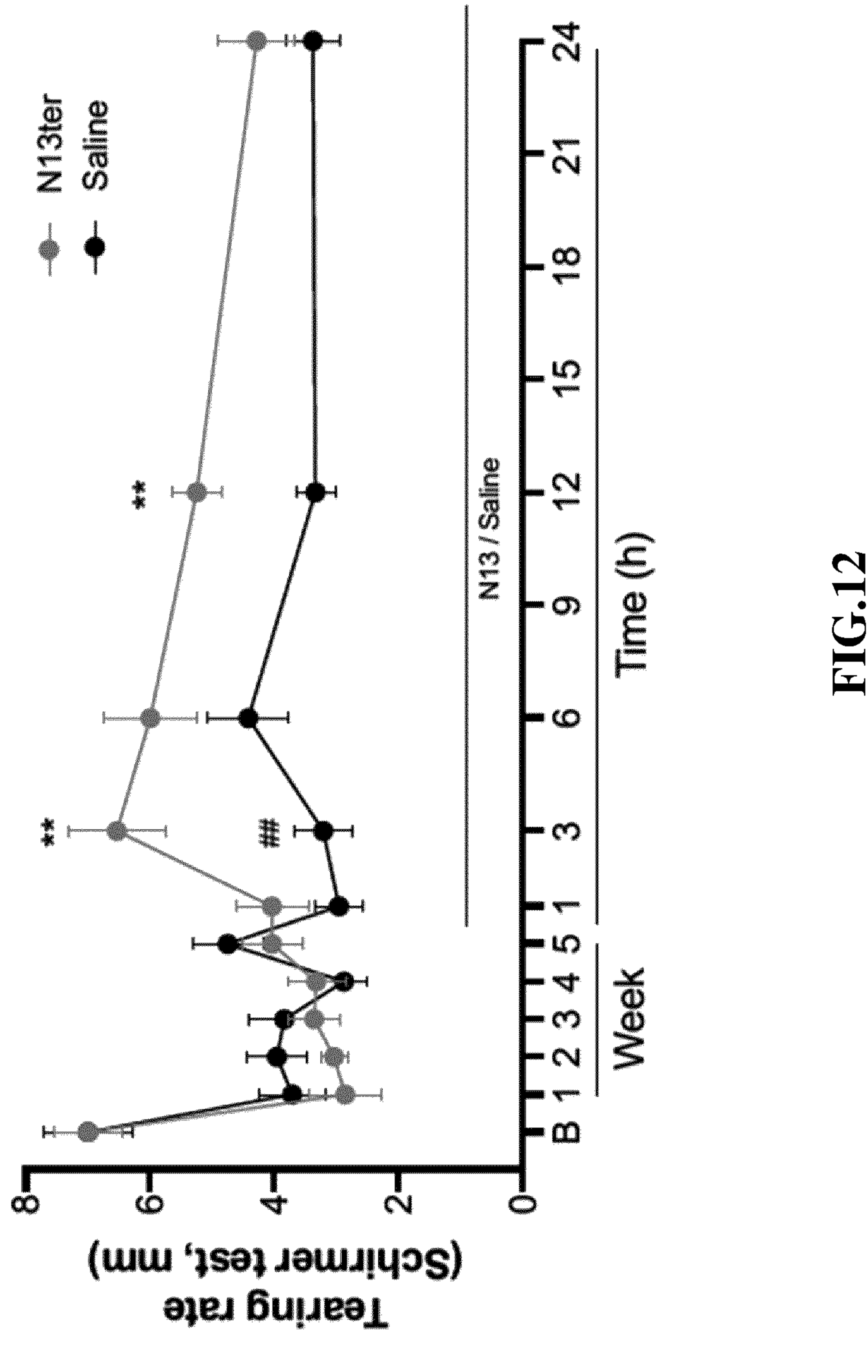

FIG. 12: Effect of N13ter peptide or vehicle on tearing rate in a dry eye model. B (Basal tearing rate before surgery). Week 1-5 (tearing rate measured at week 1, 2, 3, 4 and 5 after surgical removal of exorbital lachrymal gland). Week 5 tearing rate values were used as basal to compare with the different time points after peptide application. N13ter peptide (10 mM) or Vehicle (PBS) were topically applied at 0 h and tearing rate was measured at 1, 3, 6, 12 and 24 h. N13ter (n=14 eyes; 9 rats); Vehicle (n=12 eyes; 8 rats). **p<0.01 vs. Vehicle group; Two-way ANOVA plus Bonferroni post-tests. "p<0.01 vs. 5 Week Basal; One-way ANOVA plus Bonferroni post-tests.

DETAILED DESCRIPTION OF THE INVENTION

The inventors showed that a KCNE1 subunit interacts with TMEM16-A calcium-activated chloride channel to activate $Cl^-$ conductance, switching TMEM16-A from a calcium dependent to a voltage-dependent channel. In particular, the inventors showed that a N-terminal fragment of the KCNE1 closer to the transmembrane domain of KCNE1 recapitulates the action of KCNE1 on TMEM16-A channel $Cl^-$ conductance.

Calcium-Dependent Chloride Channel Peptide Activator

Thus, the present disclosure relates to a calcium-dependent chloride channel peptide activator also named herein TMEM16A peptide activator comprising or consisting of a functional N-terminal fragment of KCNE1 protein that binds TMEM16A and induces chloride conductance activation.

By "calcium-dependent chloride channel activator" it is intended a compound that binds on calcium-dependent chloride channel and increases $Cl^-$ conductance. According to the present disclosure, said calcium-dependent chloride channel activator binds TMEM16A and increase $Cl^-$ conductance.

Herein, the terms "peptide", "oligopeptide", "polypeptide" and "protein" are employed interchangeably and refer to a chain of amino acids linked by peptide bonds, regardless of the number of amino acids forming said chain.

The potassium voltage-gated channel subfamily E regulatory subunit 1 (KCNE1), also known as ISK, JLNS, LQT5, MinK, JLNS2 or LQT2/5 human gene (Gene ID: 3753, updated on 1 Jun. 2020) encodes a protein of 129 amino acids (NCBI reference: NP_000210.2). The TMEM16-A activator peptide according to the disclosure comprises or consists of contiguous amino acid residues between positions 30 to 38 (SEQ ID NO: 1), preferably between positions 30 to 42 (SEQ ID NO: 2) (Nter 13Peptide) of the human KCNE1 protein sequence (NCBI reference: NP_000210.2).

Since KCNE1 N-terminal fragment are well conserved, fragment originating from other animal species can be used. e.g mouse or rat KCNE1 protein. The positions of KCNE1 amino acids corresponding to those of the human KCNE1 protein can be easily identified by sequence alignments.

As for example, the TMEM16-A activator peptide comprising or consisting of contiguous amino acid residues between positions 31 to 39, preferably between 31 to 43 of the rat KCNE1 protein sequence (NCBI reference sequence: NP_0371105.1) can also be used. Advantageously, the TMEM16A peptide activator comprises or consists of human N-terminal KCNE1 fragment and bind to human TMEM16A.

In a particular embodiment, the peptide according to the present disclosure may be a functional variant of the TMEM16A peptide activator as described above.

As used herein, the term "TMEM16A peptide activator functional variant" refers to a polypeptide sequence that is derived from TMEM16A peptide activator as described above and comprises an alteration, i.e., a substitution, insertion, and/or deletion, at one or more (e.g., several) positions, but retains the capacity to activate TMEM16A channel. The variant may be obtained by various techniques well known in the art. Examples of techniques for altering the DNA sequence encoding the native protein, include, but are not limited to, site-directed mutagenesis, random mutagenesis and synthetic oligonucleotide construction.

Preferably, as used herein, the term "variant" or "functional variant" refers to a polypeptide having an amino acid sequence having at least 70, 75, 80, 85, 90, 95 or 99% sequence identity to amino acid sequence of SEQ ID NO: 1 or 2. As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al, 1997; Altschul et al., 2005). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/. Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Preferably, the term "variant" or "functional variant" refers to a polypeptide having an amino acid sequence that differs from a sequence of SEQ ID NO: 1 by less than 5, 4, 3 or 2 substitutions, insertions and/or deletions.

More preferably, the term "variant" or "functional variant" refers to a polypeptide having an amino acid sequence that differs from a sequence of SEQ ID NO: 2 by less than 6, 5, 4, 3 or 2 substitutions, insertions and/or deletions.

In particular, the functional variant is substantially homologous to amino acid sequence SEQ ID NO: 1 or 2. Two amino acid sequences are "homologous", "substantially homologous" or "substantially similar" when one or more amino acid residues are replaced by a biologically similar residue, i.e. conservative substitution.

In a preferred embodiment, the functional variant differs from the amino acid sequence of SEQ ID NO: 1 by one or more conservative substitutions, preferably by less than 5, 4, 3, or 2 conservative substitutions In a more preferred embodiment, the functional variant differs from the amino acid sequence of SEQ ID NO: 2 by one or more conservative substitutions, preferably by less than 6, 5, 4, 3, or 2 conservative substitutions.

By "substituted" or "modified" the present invention includes those amino acids that have been altered or modified from naturally occurring amino acids.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like).

Examples of conservative substitutions are within the groups of basic amino acids (arginine, lysine and histidine), acidic amino acids (glutamic acid and aspartic acid), polar amino acids (glutamine and asparagine), hydrophobic amino acids (methionine, leucine, isoleucine and valine), aromatic amino acids (phenylalanine, tryptophan and tyrosine), and small amino acids (glycine, alanine, serine and threonine).

TMEM16 peptide activator capacity of a variant to activate TMEM16A channel may be assessed by any method known by the skilled person as described above. For instance, TMEM16A activity may be assessed by patch-clamp or Two-Electrode-Voltage-Clamp (TEVC) experiments as described in examples in electrophysiology assay. In particular, the capability of a peptide functional variant to induce of voltage-dependent current as described above can be measured by patch-clamp experiments in cells, such HEK293T cells which co-express TMEM16A and said peptide or TEVC experiment on Xenopus oocytes which endogenously expressed TMEM16A.

Preferably, amino acid residues important for TMEM16A activation are conserved in the functional variant, said residue corresponds to arginine at the position 32 and/or serine at the position 38 of the human KCNE1 protein sequence (NCBI reference: NP_000210.2 accessed on Jul. 4, 2020).

In a particular embodiment, said TMEM16A peptide activator comprises or consists of a sequence L-A-R-X1-S-X2-X3-X4-X5 (SEQ ID NO: 3) wherein said

- X1 is any one of 20 amino acids, preferably arginine, lysine or histidine,
- X2 is any one of 20 amino acids, preferably proline or glutamine,
- X3 is any one of 20 amino acids, preferably arginine or leucine, and
- X4 is any one of 20 amino acids, preferably serine or arginine and,
- X5 is any one of 20 amino acids, preferably serine or aspartic acid.

In a more preferred embodiment, said TMEM16A peptide activator comprises or consists of the sequence L-A-R-X1-S-X2-X3-X4-X5-D-X6-K-L (SEQ ID NO: 4) wherein said

- X1 is any one of 20 amino acids, preferably arginine, lysine or histidine,
- X2 is any one of 20 amino acids, preferably proline or glutamine,
- X3 is any one of 20 amino acids, preferably arginine or leucine,
- X4 is any one of 20 amino acids, preferably serine or arginine,
- X5 is any one of 20 amino acids, preferably serine or aspartic acid and,
- X6 is any one of 20 amino acids, preferably glycine or serine.

In a more preferred embodiment, said TMEM16A peptide activator comprises or consists of amino acid sequence of SEQ ID NO: 1 or 2.

Preferably, the TMEM16A activator peptide as described above is of 8 to 100 amino acids residues, preferably 8 to 20 amino acids residues, more preferably 13 to 20 amino acids residues.

More preferably, the TMEM16A activator peptide is of 8 to 100 amino acids residues, preferably 8 to 20 amino acids residues, more preferably 13 to 20 amino acids residues and comprises amino acid sequence of SEQ ID NO: 1 or 2 or an amino acid sequence having at least 70, 75, 80, 85, 90, 95 or 99% sequence identity to amino acid sequence of SEQ ID NO: 1 or 2 or an amino acid sequence that differs from the amino acid sequence of SEQ ID NO: 1 or 2 by one or more conservative substitutions, preferably by less than 6, 5, 4, 3, or 2 conservative substitutions.

Peptide Preparation

Peptides described herein can be synthesized using standard synthetic methods known to those skilled in the art, for example chemical synthesis or genetic recombination.

In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloyycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; N02 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid construct comprising or consisting of a nucleic acid sequence encoding a peptide according to the disclosure, polynucleotides with nucleic acid sequences complementary to one of the above sequences and sequences hybridizing to said polynucleotides under stringent conditions.

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-0) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

For instance the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called “staple” technology described in Walensky et al, 2004. For instance, amino acids at position i and i+4 to i+7 can be substituted by non-natural amino acids that show reactive olefinic residues. All these proteolysis-resistant chemically modified peptides are encompassed in the present disclosure.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Nucleic Acid Construct and Expression Vector

The disclosure further relates to a nucleic acid encoding TMEM16A peptide activator according to the present disclosure.

In a preferred embodiment, said nucleic acid encoding TMEM16A peptide is comprised in a nucleic acid construct which further comprises regulatory sequences (such as a suitable promoter(s), enhancer(s), terminator(s), etc.) allowing the expression (e.g. transcription and translation) of a peptide according to the disclosure in a host cell.

The term “nucleic acid construct” as used herein refers to a man-made nucleic acid molecule resulting from the use of recombinant DNA technology. A nucleic acid construct is a nucleic acid molecule, either single- or double-stranded, which has been modified to contain segments of nucleic acids sequences, which are combined and juxtaposed in a manner, which would not otherwise exist in nature. A nucleic acid construct usually is a “vector”, i.e. a nucleic acid molecule which is used to deliver exogenously created DNA into a host cell.

The nucleic acid construct as described above may be contained in an expression vector. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated.

Examples of appropriate vectors include, but are not limited to, recombinant integrating or non-integrating viral vectors and vectors derived from recombinant bacteriophage DNA, plasmid DNA or cosmid DNA. Preferably, the vector is a recombinant integrating or non-integrating viral vector. Examples of recombinant viral vectors include, but not limited to, vectors derived from herpes virus, retroviruses, lentivirus, vaccinia viruses, adenoviruses, adeno-associated viruses or bovine papilloma virus.

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

The control sequence may include a promoter that is recognized by epithelial cells. The promoter contains transcriptional control sequences that mediate the expression of TMEM16A peptide activator upon introduction into a host cell. The promoter may be any polynucleotide that shows transcriptional activity in cells including mutant, truncated, and hybrid promoters. The promoter may be a constitutive or inducible promoter, preferably a constitutive promoter, and more preferably a strong constitutive promoter.

In another aspect, the invention relates to a host or host cell that expresses (or that under suitable circumstances is capable of expressing) a peptide of the disclosure; and/or that contains a nucleic acid construct of the invention. The method of producing the peptide may optionally comprise the steps of purifying said peptide, chemically modifying said peptide, and/or formulating said peptide into a pharmaceutical composition.

Pharmaceutical Composition

In a further aspect, the present disclosure also provides a pharmaceutical composition comprising a TMEM16A peptide activator, a nucleic acid or expression vector encoding said peptide as described above, and a pharmaceutically acceptable excipient.

The pharmaceutically acceptable excipient is selected according to the route of administration and the nature of the active ingredient, e.g. a peptide, a nucleic acid or a vector expression. As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolality, encapsulating agents, pH buffering substances, and buffers. Such excipients include any pharmaceutical agent suitable for direct delivery to the eye which may be administered without undue toxicity.

The pharmaceutical composition is formulated for administration by a number of routes, including but not limited to oral, parenteral and local.

The pharmaceutically acceptable carriers are those conventionally used. The pharmaceutical composition comprises a therapeutically effective amount of the peptide/polynucleotide/vector, e.g., sufficient to show benefit to the individual to whom it is administered. The pharmaceutically effective dose depends upon the composition used, the route of administration, the type of mammal (human or animal) being treated, the physical characteristics of the specific mammal under consideration, concurrent medication, and other factors, that those skilled in the medical arts will recognize.

Possible pharmaceutical compositions include those suitable for oral, rectal, topical, intraocular or parenteral administration. For these formulations, conventional excipient can be used according to techniques well known by those skilled in the art.

Preferably, the pharmaceutical composition is suitable for parenteral or ocular administration. More preferably, the pharmaceutical composition is suitable for ocular administration including topical ocular instillation and intraocular administration or transmucosal administration including nasal sprays.

Pharmaceutical compositions according to the invention may be formulated to release the active drug substantially immediately upon administration or at any predetermined time or time period after administration.

Therapeutic Use

The present disclosure also relates to the TMEM16A peptide activator, nucleic acid, expression vector according to the present disclosure for use as medicament, preferably for use for the treatment of diseases caused by chloride channel dysfunction.

Diseases caused by chloride channel dysfunction includes as non-limiting examples salivary gland dysfunction such as Sjorgen's syndrome or gland dysfunction caused by radiation injury; cystic fibrosis; gastrointestinal hypomotility disorder; cardiac arrythmia such as early repolarization syndrome; dry mouth and dry eye syndrome. Diseases caused by chloride channel dysfunction may be treatable by activating chloride channel, in particular TMEM16A channel activators.

Dry mouth due to salivary gland dysfunction is caused by multiple diseases, including Sjogren's syndrome as well as by radiation therapy for head and neck cancers and medications. Dy mouth is often associated with dysphagia, reduced taste sensation and opportunistic infections. TMEM16A channel plays an essential role for fluid secretion in salivary glands (Catalán M A, et al. Proc Natl Acad Sci USA. 2015; 112(7):2263-8).

Dry eye (keratoconjunctivis sicca) is a related disorder that is very common in the elderly, which results from lacrimal or Meibomian gland dysfunction. TMEM16A is the major ion channel regulating saliva secretion by salivary gland acinar epithelial cells (Romanenko et al., 2010. J. Biol. Chem. 285, 12990-13001).

Gastrointestinal hypomotility disorder refers to inherited or acquired changes that come with decreased contractile forces or slower transit. Gastrointestinal hypomotility disorder includes severe forms, such as pseudo-obstruction or ileus, moderate forms such as functional dyspepsia, gastroparesis, chronic constipation, and irritable bowel syndrome (IBS).

Cystic fibrosis is a genetic disease that affects the secretory epithelia of a variety of tissues. The ability of epithelial cells in the airways, liver, pancreas, small intestine, reproductive tract and other tissues to transport chloride ions, and accompanying sodium and water, is severely reduced in cystic fibrosis patients, resulting in respiratory, pancreatic and intestinal ailments. In cystic fibrosis, defective chloride transport is generally due to a mutation in a chloride channel known as the cystic fibrosis transmembrane conductance regulator (CFTR; see Riordan et al., Science 245:1066-73, 1989).

Cardiac arrhythmia is a group of conditions in which the heartbeat is irregular. According to the present disclosure, cardiac arrythmia is preferably early repolarization syndrome. Patients of early repolarization syndrome presents current imbalances between epi- and endo-cardial layers resulting in a dispersion of de- and repolarization.

The disclosure provides also a method for treating a disease caused by chloride channel dysfunction according to the present disclosure comprising administering to a patient a therapeutically effective amount of the TMEM16A peptide activator, nucleic acid, expression vector or pharmaceutical composition as described above.

By "therapeutically effective amount" refers to an amount effective, at dosages and for periods of time necessary to achieve the desired therapeutic result. The therapeutically effective amount of the product of the disclosure, or pharmaceutical composition that comprises it may vary according to factors such as the disease state, age, sex, and weight of the individual, and the ability of the product or pharmaceutical composition to elicit a desired response in the individual. Dosage regimens may be adjusted to provide the optimum therapeutic response. A therapeutically effective amount is also typically one in which any toxic or detrimental effect of the product or pharmaceutical composition is outweighed by the therapeutically beneficial effects.

As used herein, the term "patient" or "individual" denotes a mammal. Preferably, a patient or individual according to the disclosure is a human.

In the context of the disclosure, the term "treating" or "treatment", as used herein, means reversing, alleviating or inhibiting the progress of the disease caused by the chloride channel dysfunction or condition to which such term applies, or reversing, alleviating or inhibiting the progress of one or more symptoms of the disorder or condition to which such term applies.

The product of the present disclosure is generally administered according to known procedures, at dosages and for periods of time effective to induce a therapeutic effect in the patient.

The administration can be systemic or local. Systemic administration is preferably parenteral such as subcutaneous (SC), intramuscular (IM), intravascular such as intravenous (IV) or intraarterial; intraperitoneal (IP); intradermal (ID), interstitial or else. The administration may be for example by injection or perfusion. In some preferred embodiments, the administration is parenteral, preferably intravascular such as intravenous (IV) or intraarterial. The practice of the present disclosure will employ, unless otherwise indicated, conventional techniques, which are within the skill of the art. Such techniques are explained fully in the literature.

In preferred embodiment, said administration is parenteral or ocular administration. More preferably, the ocular administration including topical ocular instillation and intraocular administration is used for the treatment of dry eye syndrome and transmucosal administration including nasal sprays can be used for the treatment of cystic fibrosis.

In a further aspect, the present invention also concerns TMEM16A peptide activator, a nucleic acid, vector as described above for use to activate chloride channel, in particular TMEM16A channel, for example for in vitro diagnostic reagent, drug screening reagent or research tool to activate TMEM16A channel.

The following examples are given for purposes of illustration and not by way of limitation.

EXAMPLES

1. Experimental Model and Subject Details

Molecular Biology, Gene Expression and Cell Culture mTMEM16A (kindly provided by Dr Lily Yeh Jan) and hKCNE1 cDNA were subcloned in pIRES2eGFP, pXOOM, pcDNA3.1, pCDNA3.1-GFP and pCMV-HA vectors. Truncations and mutations on KCNE1 were generated by PCR. For SiMPull experiments, HA-tags were fused to the N-terminus of sequences, whereas GFP-tags were fused to C-terminal part. HEK293T and PCT cells were transiently co-transfected using Lipofectamine 2000 or the calcium phosphate method with a total amount of 1 and 3.5 μg of DNA, respectively, and seeded on 18 mm diameter coverslips. HEK cells were maintained in DMEM with 5% FBS on poly-L-lysine-coated glass coverslips in 12 well plates. PCT cells from wild type and knock-out mice were microdissected as described previously and maintained in F12 (Gibco) on collagen-coated glass coverslips.

Electrophysiology

HEK293T and PCT cell electrophysiology was performed 24-48 h after transfection. For whole-cell patch-clamp experiments cells were recorded in a bath solution containing (in mM) 150 NaCl, 5 KCl, 2 $CaCl_2$ and 10 HEPES, pH 7.4 and 0.05% BSA. The glass pipettes (2-5 MΩ of resistance) were filled with (in mM) 5 NaCl, 135 CsCl, 2 $MgCl_2$, 5 EGTA, 10 HEPES, pH 7.3. Cells were recorded either after incubation of 30 min with the peptide or during perfusion with the peptide. Total calcium concentration was calculated with Maxchelator (maxchelator.standford.edu) for a temperature of 20° C. HEK293T and PCT cells were recorded at room temperature in voltage-clamp mode using an Axopatch 200A (Molecular Devices) amplifier. Signals were filtered at 10 kHz and digitalized at 20 kHz. Whole-cell currents were elicited by voltage-ramps (from −100 to +100 mV, 1 s) and I-V stimulation pulses (from −100 to +100 mV in 20 mV increments, 1 s each pulse), holding the cells at −80 mV. Current densities were measured at +100 mV. Cell recordings, data acquisition and analysis of electrophysiology experiments were performed using pClamp software (Molecular Devices).

Oocyte currents measurements were made using two standard microelectrodes (1-2.5 MΩ resistance) filled with 3 M KCl and maintained under voltage-clamp using a Dagan TEV 200 amplifier in a standard ND96 solution (in mM: 96 NaCl, 2 KCl, 1.8 CaCl2, 1 MgCl2, 10 HEPES, pH 7.4) with 0.05% BSA. Currents were elicited using the same voltage-ramp protocol described above.

Peptide Design

Peptides were ordered by Genscript, following the sequence of interest. The quantity ranged from 4 to 20 mg, with a purity of ≥80% (upgrade to ≥85%) and aliquoted in one single vial. An additional solubility test of ultrapure water, DPBS (pH 7.1) and DMSO was asked before their ordering. Finally, peptides were diluted in ultrapure water.

Single Molecule Pulldown Assay

For SiMPull assays, the inventors followed the protocol previously described by Jain et al., 2011. Nature 473, 484-488. Briefly, HEK293T cells co-transfected with an HA-tagged bait protein and a GFP-fused prey protein (applying the widely used eGFP A206K mutant which greatly reduces homodimerization events) were lysed in a buffer containing (in mM): 150 NaCl, 10 Tris pH 7.5, 1 EDTA, protease inhibitor cocktail (Thermo Scientific) and 1.5% IGEPAL (Sigma). Lysates were collected and pulled-down on coverslips passivated with PEG (99%) and biotin-PEG (1%) and treated with neutravidin (1.4 mg/mL, Pierce) and biotinylated anti-HA antibody (15 nM, abcam, #ab26228). Several washes with T50 buffer (in mM: 50 NaCl, 10 Tris, 20 EDTA; 0.1 mg/mL BSA, pH 7.5) were performed to avoid unspecific protein binding. Finally, single molecule complexes were imaged using a 488 nm Argon laser in total internal reflection fluorescence microscopy with a 100× objective (Olympus). 13×13 μm2 movies of 250 frames were acquired at frame rates of 10-30 Hz and analyzed using Fiji software (NIH). Multiple independent experiments were performed for each condition and only the spots which were fully bleached at the end of the illumination were considered. Representative data sets are presented to quantitatively compare the different conditions (minimum 15 movies per condition, at least analyzed traces per movie).

Animals

Sprague-Dawley rats (males, around 200 g) were purchased from Charles River and adapted one week before processing the experiment. Two-three rats per cage were housed in a controlled environment of 12 hours intervals of light/dark cycles and free access to food and water. Animal experiments were approved by the Animal Care and Use Committee of the University of Barcelona (CEEA) and the Departament de Territori i Sostenibilitat of Generalitat de Catalunya, Catalonia, Spain (319/19; 10935) and followed the ethical guidelines of the International Association for the Study of Pain.

Peptides

N13ter (also named Nter 13 peptide or N13) (LARRSPRSSDGKL (SEQ ID NO: 2)) and scramble (LLAKRGRDSGPSR (SEQ ID NO: 7)) peptides were purchased from GenScript Biotech (Leiden, Netherlands) and provided by CNRS. Both peptides were dissolved in Phosphate Buffered Saline (PBS) at 10 mM and used for topical ocular application (5 ul per eye).

Measurement of Tear Fluid Secretion

Tear fluid secretion (tearing rate) was measured using phenol red threads (Zone-Quick, Menicon, Nagoya, Japan)

placed on the lower eyelid for 30 s without topical anesthesia (Trost, 2007; Acosta 2013). Tearing rate was determined with an accuracy of ±0.5 mm by measurement of the length of the red portion of the thread.

Acute Effects of Vehicle, Positive Control, N13ter or Scramble Peptides

After habituation of the animals, basal tearing rate was measured in both eyes before any topical application of peptides. Then, animals were divided in different groups and a solution containing vehicle (PBS), amiloride (1 mM), peptide N13 or peptide scramble was topically applied to the ocular surface (5 μl) and tearing rate was measured at 1, 3, 6, 12 and 24 h. Tearing rate measurements were done blind to the treatment received by the animals.

Dry Eye Animal Model

To establish a dry eye model, a similar procedure to those previously described was used (Callejo 2015, Pain; 156(3): 483-495, Kovacs, 2016, Pain.; 157(2):399-417). Rats were intraperitoneally anaesthetized with ketamine/xylacine (80: 10 mg/kg). Surgical bilateral removal of the main lachrymal gland (exorbital) was done after performing a skin incision on the temporal side, posterior to the lateral canthus. The fibrous capsule of the exorbital gland was exposed and dissected, and the lachrymal gland carefully excised. At the conclusion of the surgery, a drop of antibiotic/anti-inflammatory solution (3 mg/ml gentamicin; 0.5 mg/ml dexamethasone; Colircusi Gentadexa; NTC Ophthalmics, Spain) was applied onto the surgical area. The skin incision was sutured using 5-0 silk braided suture. Animals were housed individually, and conjunctival and corneal appearance was checked regularly. Tear fluid secretion was measured in both eyes before (basal) and once a week at 1, 2, 3 and 4 weeks after surgery using phenol red threads (Zone-Quick, Menicon, Nagoya, Japan) placed on the lower eyelid for 30 s without topical anesthesia (Trost, 2007; Acosta 2013). Tearing rate was determined with an accuracy of ±0.5 mm by measurement of the length of the red portion of the thread. After tearing rate measurement on week 4, animals were divided in two groups and a solution containing one of the peptides (N13ter or PBS) was topically applied to the ocular surface (5 μl) and tearing rate was measured at 1, 3, 6, 12 and 24 h. Tearing rate measurements were done blind to the treatment received. Eyes that did not present a decreased tear volume (dryness) on week 4 or presented some kind or inflammation or redness indicative of possible ocular disease, were excluded from the study.

Data Analysis

Data are presented as mean±standard error of the mean (SEM). Statistical differences between different sets of data were assessed by performing repeated measured One-way ANOVA plus Bonferroni's post-tests (each data point in an experimental group vs. basal values) or repeated measured Two-way ANOVA plus Bonferroni's post-tests (each data point in N13ter group vs. Scramble or Vehicle group; or point in N13ter or amiloride groups vs. Vehicle group) using Prism 9 (GraphPad Software, San Diego, CA). The significance level was set at $p<0.05$ in all statistical analyses.

2. Results

KCNE1 Shifts TMEM16A from a Calcium Dependent to a Voltage-Dependent $Cl^-$ Channel To test the ability of KCNE1 to regulate TMEM16A, the inventors used the HEK293T cell model which does not express neither TMEM16A nor KCNE1 endogenously. Whereas transfection of HEK293T cells with either TMEM16A or KCNE1 alone produced no significant current, co-expression of both proteins induced a voltage-dependent current, whose density was of 18.1±2.8 pA/pF at +100 mV (FIGS. 1A and 1B). The reversal potential was −4.8±1.3 mV, which is similar to the expected reversal $Cl^-$ potential in the experimental conditions used. This chloride current was inhibited by NFA, T16Ainh-A01 (Davis, A. J. et al. 2013. Br J Pharmacol. 168, 773-784) and also by Ani9, the most specific TMEM16A inhibitor (Seo, Y. et al. 2016, PLoS One 11, e0155771) (FIGS. 1C-E). This suggests that KCNE1 switches TMEM16A from a calcium-dependent to a voltage-dependent chloride channel.

To preclude the possibility that KCNE1 activates endogenous calcium channels, the inventors conducted similar experiments in the presence of the fast calcium chelator BAPTA. As shown in FIG. 1F, BAPTA did not abolish the formation of the voltage-dependent current evoked by co-expression of both proteins (3.70±0.41 pA/pF vs 21.98±5.32 pA/pF in the absence or presence of BAPTA, $P<0.001$). To totally rule out a potential modulation of endogenous calcium channels by KCNE1 leading to the TMEM16A activation, the inventors co-expressed KCNE1 with the $Ca^{2+}$-activated SK4 channel, which has similar calcium sensitivity (Cao, Y. J., and Houamed, K. M. 1999. FEBS Lett 446, 137-141) as TMEM16A. As shown in FIG. 2, KCNE1 overexpression did not induce any increase of the SK4 current in absence of calcium. Altogether, these results exclude an implication of intracellular $Ca^{2+}$ in a KCNE1-induced activation of TMEM16A.

TMEM16A Activation by KCNE1 Involves Physical Interaction

To be considered as auxiliary subunit, a protein has to interact directly and stably with the α-subunits. To test the physical association between TMEM16A and KCNE1, the inventor used the recently developed single molecule pull-down (SiMPull) assay (Jain, A. et al. 2011. Nature. 473, 484-488; Levitz, J. et al. 2016. Proc Natl Acad Sci USA. 113, 4194-4199; Royal, P. et al. 2019. Neuron. 101, 232-245.e236). This technique enables direct visualization of antibody-immobilized protein complexes (FIGS. 3A and 3E) allowing to determine the composition and stoichiometry within single protein complexes by counting fluorophore bleaching (Jain, A. et al. 2011. Nature. 473, 484-488; Levitz, J. et al. 2016. Proc Natl Acad Sci USA. 113, 4194-4199; Royal, P. et al. 2019. Neuron. 101, 232-245.e236). After co-transfection with the two putative partners KCNE1 and TMEM16A, one of them fused with an HA affinity tag and the other with a GFP label, and subsequent pull-down, the inventors observed many fluorescent spots for both conditions, TMEM16A-GFP+HA-KCNE1 (FIG. 3B) and KCNE1-GFP+HA-TMEM16A (FIG. 3F). This demonstrates a physical interaction between KCNE1 and TMEM16A. Importantly, when HA-KCNE1 or HA-TMEM16A were not co-expressed, no proteins fused to GFP were isolated (FIGS. 3J and 3L), confirming the specificity of the HA-antibody used in SiMPull assays. By analyzing bleaching steps for immobilized HA-KCNE1-TMEM16A-GFP complexes, the inventors were able to determine the number of TMEM16A-GFP subunits within the complex. They found that the majority of fluorescence intensity trajectories showed two-step bleaching (~70%), with the remaining spots bleaching in one step (~20%) or occasionally three steps (~10%) (FIGS. 3C and 2D). This distribution agrees well with the binomial distribution predicted for a strict dimer based on an estimated GFP maturation probability of ~75% (Ulbrich, M. H., and Isacoff, E. Y. Nat Methods, 4, 319-2 321; Zacharias, D. A. et al. 2002. Science, 296, 913-916). Analysis of the SiMPull experiment with HA-TMEM16A-KCNE1-GFP showed that most complexes presented two bleaching steps (~65%) and some remaining spots bleached in one (~25%) and three steps (~10%) (FIGS. 3G and 3H). This distribution corresponds to the presence of two KCNE1-GFP subunits within the protein complex. Therefore, two KCNE1 subunits assemble with a single TMEM16A channel (Dang, S. et al. 2017. Nature. 552, 426-429; Takumi, T. et al. 1988. Science, 242, 1042-1045), following a 2α:2β stoichiometry.

The Complex KCNE1-TMEM16A Generates Voltage-Dependent $Cl^-$ Currents in Proximal Convoluted Tubule Cells To be considered as a bona fide auxiliary subunit, the protein must interact with alpha subunits in a native environment. To confirm that KCNE1 is an auxiliary subunit of TMEM16A in native tissue and to eliminate possible artifacts due to heterologous overexpression, the inventors took advantage of kidney proximal convoluted tubule (PCT) cells obtained from wild type and kcne1 KO mice (Barrière, H. et al. 2003. J Membr Biol. 193, 153-170). PCT cells are considered as a relevant model as they naturally co-express both TMEM16A and KCNE1 (Faria, D. et al. 2014. Kidney Int. 85, 1369-1381; Vallon, V et al. 2001. J Am Soc Nephrol, 12, 2003-2011) and do not necessitate any genetic manipulation to record TMEM16A channel carried currents. Moreover, while no modification of the $K^+$ current was found in PCT cells from kcne1 KO mice compared to wild type, a DIDS (4,4'-Diisothiocyanostilbene-2,2'-disulfonic acid)-sensitive $Cl^-$ conductance was impaired (Barrière al., 2003). The inventors confirmed the loss of current, whose reversal potential was similar to the expected $Cl^-$ reversal potential in kcne1 null PCT cells (18.07±1.21 pA/pF vs 5.37±0.56 pA/pF for PCT wild type and KO mice, respectively, P<0.001) (FIG. 4A). This current was inhibited by NFA (4.51±0.28 pA/pF), T16A(inh)-A01 (5.52±0.72 pA/pF) and Ani9 (2.88±0.38 pA/pF) (FIG. 4B-D). Moreover, knock-down of TMEM16A by a previously validated siRNA transfection (Sala-Rabanal, M. et al. 2017. J Biol Chem, 292, 9164-9174) in wild type PCT cells significantly reduced the $Cl^-$ current amplitude (4.23±0.48 pA/pF) (FIG. 4E). This demonstrates the involvement of TMEM16A subunits in the channel complex responsible for the herein studied $Cl^-$ current. A rescue experiment by KCNE1 transfection in $kcne1^{-/-}$ cells fully restored the voltage-dependent $Cl^-$ current (21.59±1.38 pA/pF) (FIG. 4F), showing that the absence of chloride current in these cells was only due to the KO of kcne1 and not due to any modification that might occur during the culture process.

The N-Terminal Pre-Transmembrane Domain of KCNE1 is a Key for TMEM16A Regulation KCNE1 is a single transmembrane protein with an extracellular N-terminal part and a C-terminal domain within the cytosol (Takumi, T. et al. 1988. Science, 242, 1042-1045). To determine the interacting site with TMEM16A, the inventors produced a series of truncated KCNE1 forms (FIG. 5A) and tested them for their ability to regulate TMEM16A. Truncation of the full KCNE1 C-terminal domain did not abolish the KCNE1-mediated TMEM16A regulation (25.04±4.9 pA/pF, P>0.15) (FIG. 5B). By contrast, deletion of the full N-terminal domain suppressed the ability of KCNE1 to regulate TMEM16A (6.56±0.89 pA/pF, P<0.001) (FIG. 5B). No effect was observed for the partial N-terminal truncation ΔNt16 (25.43±4.46 pA/pF) nor ΔNt30 (25.23±6.62 pA/pF) (FIG. 5C), demonstrating that the sequence of 13 residues (from L30 to L42) preceding the transmembrane domain is essential for TMEM16A activation. This result is in line with the previous observation, that a partial deletion of KCNE1, including eight of the 13 amino acids (KCNE1Δ11-38) abolished the KCNE1-induced chloride current in Xenopus oocytes (Attali, B et al. 1993. Nature, 365, 850-852). To check if this small domain is sufficient to recapitulate the properties of the entire KCNE1 on the TMEM16A current, the inventors used a corresponding synthetic peptide (Nter13), bearing the L30-L42 sequence. In HEK293T cells expressing TMEM16A, application of 100 μM Nter13 elicited an Ani9 sensitive current (15.48±3.25 pA/pF) (FIG. 5D; FIGS. 6A and 6B). Again, the reversal potential was similar to the current observed when KCNE1 is co-expressed, whereas no effect was observed for an application of scrambled peptide (FIG. 5D).

KCNE1 Polymorphisms Inside the TMEM16A-Regulating Sequence Suppress the $Cl^-$ Current Within the 13-residues extracellular domain of KCNE1, previous works have shown that the common S38G and R32H polymorphisms, which are not or just poorly affecting the KCNE1-mediated regulation of KCNQ1 (FIGS. 7A and 7B) (Westenskow et al., 2004; Yao et al., 2018), may be related to cardiac arrhythmia (Crump, S. M., and Abbott, G. W. 2014. Front Genet 5, 3). The inventors therefore tested the potential of these two KCNE1 variants to regulate TMEM16A. The related disease mutation T7I, which is not in the regulating domain, was used as a control. Whereas mutation T7I did not alter the KCNE1-dependent regulation of TMEM16A (24.69±1.57 pA/pF, P>0.4) (FIGS. 7C and 7D), both mutations R32H and S38G abolished the ability of KCNE1 to modulate the TMEM16A current properties (5.69±1.18 pA/pF and 6.96±0.78 pA/pF for R32H and S38G, respectively) (FIGS. 7C and 7D) suggesting a potential implication of the KCNE1-KCNQ1 in human diseases.

In HEK293T cells expressing TMEM16A, although application of 100 μM human Nter13 peptide induces TMEM16A current properties, peptide N13 presenting S38G polymorphism has no effect on the TMEM16A current properties (FIG. 8).

The human Nter13 peptide is more potent than rat N13 peptide on TMEM16A (FIG. 9). In fact, at 100 μM the rat N13 peptide presents only a small effect on TMEM16 (FIG. 9).

Discussion

Most of ion channels are assembled as complexes of a pore forming α-subunit, associated with auxiliary (β) subunits. In this study, the inventors demonstrate that KCNE1, which is classically considered a β-subunit of the cardiac KCNQ1 pore-forming subunit belonging to the voltage-dependent Kv channel superfamily, serves also as an auxiliary subunit of the anoctamin superfamily channel TMEM16A, a $Ca^{2+}$-activated $Cl^-$ channel (CaCC). By interacting stably with TMEM16A following a 2α:2β stoichiometry, KCNE1 induces a voltage-dependent current in the absence of intracellular elevation of calcium. KCNE1 polymorphisms within the TMEM16A-interacting domain abolish its ability to regulate TMEM16A, suggesting a possible implication of this voltage-dependent chloride current in human diseases. β-subunits of ion channels provide an important source of diversity of electrical signaling molecular players in cells. Although they cannot induce native currents per se, they associate with pore-forming subunits of ion channels and modulate their pharmacological and biophysical characteristics. Their physiological importance is reflected by the large number of diseases linked to their mutations, such as muscular pathologies, epilepsy and cardiac arrhythmias (Adelman, 1995, Curr Opin Neurobiol. 5, 286-295; Cannon, 2007, Neurotherapeutics. 4, 174-183; Crump and Abbott, 2014, Front Genet. 5, 3; Vergult et al., 2015, Eur J Hum Genet. 23, 628-632). KCNE1 is a famous example of a $K_v$ β-subunit, which associates with KCNQ1 and hERG to control both $I_{Ks}$ and $I_{Kr}$ components of the cardiac action potential and for which more than sixty gene variants have been reported to be associated with human diseases, particularly with cardiac arrhythmias (Barhanin et al., 1996, Nature. 384, 78-80; Crump and Abbott, 2014, Front Genet. 5, 3; Sanguinetti et al., 1996, Nature. 384, 80-83; Sanguinetti et al., 1995, Cell. 81, 299-307). Cross-modulation by β-subunits of pore-forming-α-subunits from the same superfamily of ion channels was shown for $Na_V$ and $K_V$ channels (Marionneau et al., 2012. J Neurosci. 32, 5716-5727; Nguyen et al., 2012. Proc Natl Acad Sci USA. 109, 18577-18582). $Na_v\beta_1$ was found to coordinate control of $K_v$ and $Na_v$ channels which derivate from the same ancestor (Moran et al., 2015, J Exp Biol. 218, 515-525) and belong to the superfamily of voltage-gated ion channels. The results demonstrate cross-modulation of two different superfamilies which are not phylogenetically related: the voltage-gated channels and the anoctamins. The inventors found that, by interacting with TMEM16A, KCNE1 modifies the gating of this member of the anoctamin superfamily, switching it from a calcium-dependent to a voltage-dependent channel. The experiments with different $Ca^{2+}$ chelators and with a $Ca^{2+}$-activated SK channel as a very sensitive reporter demonstrated that activation of this CaCC is independent of any rise of cytosolic $Ca^{2+}$, the natural activator of the channel in the absence of KCNE1 (Caputo et al., 2008. Science 322, 590-594; Schroeder et al., 2008. Cell 134, 1019-1029; Yang et al., 2008. Nature 455, 1210-1215). Clearly, the voltage-dependent chloride channel superfamily is not restricted to the ClC family, but extends to the anoctamin family when combined with KCNE1. This also shows that the difference between $Ca^{2+}$ and voltage-dependent channels is not so strict and that one should rather consider a continuum of biophysical properties.

Whereas the KCNQ1-KCNE1 stoichiometry remains a matter of debate (Morin and Kobertz, 2008. Proc Natl Acad Sci USA. 105, 1478-1482; Murray et al., 2016. Elife. 5; Nakajo et al., 2010. Proc Natl Acad Sci USA. 107, 18862-18867; Plant et al., 2014. Proc Natl Acad Sci USA. 111, E1438-1446), the inventors found by using the SiMPull assay (Jain et al., 2011. Nature. 473, 484-488; Levitz et al., 2016. Proc Natl Acad Sci USA. 113, 4194-4199; Royal et al., 2019. Neuron. 101, 232-245.e236), that the TMEM16A-KCNE1 complex is composed of 2α:2β subunits. The inventors have shown that this complex takes place in HEK cells upon heterologous expression, but also show that it is present in native kidney cells, where it mediates a $Cl^-$ conductance, which is sensitive to TMEM16A inhibitors. This $Cl^-$ conductance cannot be recorded in KCNE1 knock-out cells or in cell in which KCNE1 has been knock-down, and it is rescued in these cells by KCNE1 re-expression upon transfection. Therefore, the TMEM16A-KCNE1 association is not to only found upon recombinant over-expression, but can be observed in native cells where it participates in the maintenance of the resting membrane potential.

The electrophysiological assays, using truncated forms of KCNE1 and synthetic peptides based on the β-subunit, allowed to determine the crucial role of the N-terminus of KCNE1 in TMEM16A regulation. More specifically, the inventors have observed that the segment closer to the transmembrane domain of KCNE1 is necessary and sufficient to recapitulate the action of the entire KCNE1 on the TMEM16A current. The synthetic peptide generated on the basis of this segment's sequence is the first designed TMEM16A agonist and may be useful for clinical applications. Notably, activation of an apical chloride channel such as TMEM16A triggers the secretion of water, which makes TMEM16A-targeted activators potential drug candidates for treatment of cystic fibrosis or dry eyes syndromes.

This 13 amino acid segment bears at least two residues which are subject to polymorphisms (R32H and S38G) related with cardiac arrhythmias (Crump and Abbott, 2014. Front Genet 5, 3).

Whereas several clinically relevant KCNE1 variants were found to modify its ability to regulate KCNQ1, providing a link between these mutations and polymorphisms with cardiac arrhythmias, the KCNE1 S38G poorly impairs KCNQ1 regulation by KCNE1 (Yao et al., 2018. Exp Cell Res 18 363, 315-320). The inventors found that the KCNE1 S38G as well as the R32H mutants, lost their ability to regulate TMEM16A, suggesting a potential role of this chloride current in cardiac arrhythmias.

Along this line, a recent study performed in canine heart suggests a protective role for TMEM16A against risk of arrhythmias by reducing spatial and temporal heterogeneity of cardiac repolarization and early after depolarization (Hegyi et al., 2017. Ca. J Mol Cell Cardiol 109, 27-37).

To sum up, the inventors have found that KCNE1, a well-known auxiliary subunit of voltage-dependent $K^+$ channels, meets the four needed conditions to be considered as an auxiliary subunit of the anoctamin anion channel superfamily (Adelman, 1995. Curr Opin Neurobiol. 5, 286-295; Arikkath and Campbell, 2003. Curr Opin Neurobiol. 13, 298-307. J Biol Chem. 271, 27975-27978; Cannon, 2007. Neurotherapeutics. 4, 174-183; Gurnett and Campbell, 1996. Neuron. 7, 403-408; Trimmer, 1998. Curr Opin Neurobiol. 8, 370-374): first, KCNE1 does not show any ion channel activity by itself, second, KCNE1 and TMEM16A interact directly and stably with a fixed stoichiometry (2α:2β), third, KCNE1 modifies drastically the TMEM16A function enabling the channel to work in the absence of elevated cytosolic calcium, and fourth, KCNE1 regulates TMEM16A in native tissue. Therefore, KCNE1 fulfills all the criteria of a bona fide auxiliary subunit of two distinct classes of ion channel superfamilies which are not phylogenetically related: voltage-gated cation channels and anoctamin superfamilies. Finally, the TMEM16A-KCNE1 association should be considered when analyzing outcomes of clinically relevant KCNE1 mutations, as emphasized by the finding that two known cardiac arrhythmia related KCNE1 variants, including S38G, lost their ability to regulate TMEM16A.

Study on the N13 Peptide for Ocular Tearing Eye a) Acute Effect of N13ter on Tear Fluid Secretion The effects of peptides were evaluated in 20 eyes of 10 rats for each experimental group (N13ter and Scramble). As none of the rats presented any alteration in the external ocular structures or any sign of irritation, infection or inflammation, all eyes were included in the study. Basal tearing rate was 7.65±0.49 mm for N13ter and 8.10±0.54 mm for Scramble group (n=20 eyes; 10 animals, respectively). N13ter application produced a small but significant increase in tearing rate compared with Scramble application (Two-way ANOVA: p=0.0027). Post-hoc Bonferroni's post tests showed significant differences at 6 h (9.65±0.57 mm; *p<0.05) and 12 h (8.85±0.73 mm; *p<0.05) time-points compared to Scramble group. When the different time points were compared to the basal value, a significant difference was obtained at 6 h (#p<0.05; One-way ANOVA plus Bonferroni post-tests).

The Scramble group produced a sustained small decrease compared to basal values and to the N13ter group. A significant difference was obtained at 12 h (6.45±0.34 mm;

#p<0.05; One-way ANOVA plus Bonferroni post-tests) when comparing to the basal value. Data suggests that N13ter application have an enhancing effect on tearing rate when compared to scramble peptide and that this effect becomes significant after 6-12 h of peptide application. Although not significant, values obtained 24 h after application had not recovered completely basal values, suggesting some long-lasting effects of the treatment.

The effects of vehicle and amiloride (positive control) were evaluated in 14 eyes of 7 rats for each experimental group (vehicle and amiloride). A group testing the N13ter peptide were done in parallel in 12 eyes of 6 rats, in the same conditions as done in the previous study. As none of the rats presented any alteration in the external ocular structures or any sign of irritation, infection, or inflammation all eyes were included in the study. Basal tearing rate was 5.06±0.38 mm for Vehicle group, 4.78±0.56 mm for amiloride and 4.53±0.43 for N13ter group (n=14, 14 and 12 eyes, respectively).

N13ter application produced a significant increase in tearing rate compared with Vehicle application (Two-way ANOVA: p=0.029). Post-hoc Bonferroni's post tests showed significant differences at 12 h (6.66±0.64 mm; *p<0.05) time-point, compared to Vehicle group. When the different time points were compared to the basal value, a significant difference was obtained at 12 h (#p<0.05; One-way ANOVA plus Bonferroni post-tests). No significant effects were found when comparing vehicle values at the different time points to basal value, indicating a lack of effect of vehicle application.

Amiloride application produced a transient effect of increasing tearing rate, which peaked at 3 h (5.89±0.0.23 mm; n=14). Among the eyes tested, in 7 out of 14 eyes amiloride increased tearing rate between 1 h to 3 h, although in other 2 eyes did not induce any effect or slightly decrease tearing rate. Comparison to vehicle group did not show a statistically significant effect, probably due to some dispersion of the data, as well as the multiple comparisons performed, which diminishes statistical power.

To compare and to minimize differences due to other variables (batch of animals, time of the year of the study, etc.), data has been normalized to the basal value for each eye (basal tearing rate has been considered 100% and other values calculated accordingly) and averaged for each experimental group in FIGS. 10A and B. The enhancing effect develops between 2-6 h after topical application. Tearing rate remains elevated for several hours before returning to basal levels. In contrast, vehicle application (PBS) did not produce significant effects in any direction As experiments to test the effects of N13ter peptide performed were done following the same protocol, all data has been pulled together in a single group as shown in FIG. 11. Comparison with the vehicle group shows a statistically significant effect at 1, 3, 6, 12 and 24 h, obtaining the maximal increase at 6 and 12 h (FIG. 11).

In conclusion, N13 peptide appears to exert an enhancing effect on tearing rate when topically applied to the ocular surface of rat. This enhancing effect lasts several hours and some effects are still present after 24 h.

Effect of N13ter and Vehicle on Tear Fluid Secretion in a Dry Eye Model

The effects of peptides were evaluated in 14 eyes (9 rats) for N13ter and 12 eyes (8 rats) for vehicle group. Tearing rate was measured at 5 weeks, before topical application of N13ter (10 mM) or vehicle (PBS). After 5 weeks of surgery, tearing rate values (5 weeks Basal) remained at similar values than precedent weeks (4.04±0.49 mm for N13ter and 4.75±0.58 mm for vehicle group), indicating that ocular dryness remained at similar levels. As shown in FIG. 12, N13ter application produced a similar effect than in the previous experiment which was statistically significant compared to vehicle group (Two-way ANOVA: p=0.0044). After N13ter application, a progressive increase in tearing rate was observed that peaked at 3 h (6.54±0.78 mm; "p<0.01 vs. Vehicle; Two-way ANOVA plus Bonferroni post-tests) and stayed above basal levels for several hours before returning to basal values within 24 h. Analysis of the data with a repeated measures one-way ANOVA test vs. 5 week basal values indicated a significant difference (p=0.0277) although Bonferroni's post-tests did not indicate significant differences at each time point, probably due to the statistical power needed and some dispersion of the data. On the contrary, vehicle application produced an initial decrease in tearing rate that slightly recover basal values (5 weeks data point) and remained stable for the rest of the experiment. A repeated measures one-way ANOVA test vs. 5 weeks basal values did not show a significant difference although the value was really close (p=0.0517) and Bonferroni's post-tests indicated a significant difference at 3 h (3.21±0.47 mm; np<0.01). Data show that an enhancement of tearing rate occurs after the application of N13ter while vehicle application seems to produce opposite effects on tearing rate.

In conclusion, the N13ter peptide appears to exert an enhancing effect on tearing rate when topically applied to the ocular surface of rats, both in naive animals and in animals that had developed ocular dryness.

The invention claimed is:

1. A pharmaceutical composition comprising PBS with a TMEM16A peptide activator consisting of an amino acid sequence L-A-R-R-S-P-R-S-S-D-G-K-L (SEQ ID NO: 2), wherein the TMEM16A peptide activator has a concentration of 10 mM or 100 μm.

* * * * *